US012793856B2

(12) United States Patent
Noshay et al.

(10) Patent No.: US 12,793,856 B2
(45) Date of Patent: Nov. 10, 2026

(54) CHRONIC KIDNEY DISEASE (CKD) MACHINE LEARNING PREDICTION SYSTEM, METHODS, AND APPARATUS

(71) Applicants: Vantive US Healthcare LLC, Deerfield, IL (US); Vantive Health GmbH, Glattpark (CH)

(72) Inventors: Eric David Noshay, Glenview, IL (US); AnnaLisa Daniele, Chicago, IL (US); Angela Sofia Rivera Florez, Port St. Lucie, FL (US); Yukun Chen, Irving, TX (US); Michael Seeber, Irving, TX (US)

(73) Assignees: Vantive US Healthcare LLC, Deerfield, IL (US); Vantive Health GmbH, Glattpark (CH)

( * ) Notice: Subject to any disclaimer, the term of this patent is extended or adjusted under 35 U.S.C. 154(b) by 1097 days.

(21) Appl. No.: 17/481,429

(22) Filed: Sep. 22, 2021

(65) Prior Publication Data

US 2022/0093261 A1 Mar. 24, 2022

Related U.S. Application Data

(60) Provisional application No. 63/082,017, filed on Sep. 23, 2020.

(51) Int. Cl.
*G16H 50/30* (2018.01)
*G06N 20/20* (2019.01)
(Continued)

(52) U.S. Cl.
CPC ............. *G16H 50/30* (2018.01); *G06N 20/20* (2019.01); *G16H 10/60* (2018.01); *G16H 20/40* (2018.01); *G16H 50/20* (2018.01)

(58) Field of Classification Search
CPC .......... G06N 20/20; G06N 20/00; G06N 7/01; G16H 50/30; G16H 20/40; G16H 10/60; G16H 50/20
See application file for complete search history.

(56) References Cited

U.S. PATENT DOCUMENTS

2016/0189210 A1* 6/2016 Lacey .................. G06Q 10/067 705/7.31
2019/0046112 A1 2/2019 Blanchard et al.
(Continued)

OTHER PUBLICATIONS

Dovgan, Erik, et al. "Using machine learning models to predict the initiation of renal replacement therapy among chronic kidney disease patients." Plos one 15.6 (2020): e0233976. (Year: 2020).*
(Continued)

*Primary Examiner* — Andrew T Chiusano
(74) *Attorney, Agent, or Firm* — K&L Gates LLP

(57) ABSTRACT

A chronic kidney disease ("CKD") machine learning prediction system is disclosed. The example system is configured to provide a projection as to whether a patient may progress to a next stage of CKD and/or whether the patient may need to urgently start dialysis. The machine learning algorithms disclosed herein include dynamic, multifactorial predictive algorithms that are programmed to consider clinical, pharmacological, and extra-clinical factors that adversely impact kidney function. The predictions provided by the machine learning system convey information to clinicians for improving CKD treatment before the disease worsens. In some instances, the predictions may be used for selecting a treatment plan, a dialysis treatment, and/or a renal replacement therapy ("RRT").

20 Claims, 8 Drawing Sheets

(51) Int. Cl.

| | |
|---|---|
| ***G16H 10/60*** | (2018.01) |
| ***G16H 20/40*** | (2018.01) |
| ***G16H 50/20*** | (2018.01) |

(56) References Cited

U.S. PATENT DOCUMENTS

| | | | | |
|---|---|---|---|---|
| 2020/0005900 | A1 | 1/2020 | Cha et al. | |
| 2021/0118570 | A1* | 4/2021 | Petrich | G06N 3/08 |
| 2021/0327589 | A1* | 10/2021 | Bradley | G06F 18/214 |
| 2024/0355477 | A1* | 10/2024 | McNair | G06Q 10/1095 |

OTHER PUBLICATIONS

Tangri, Navdeep, et al. "A dynamic predictive model for progression of CKD." American Journal of Kidney Diseases 69.4 (2017): 514-520. (Year: 2017).*

Panwong, Patcharaporn, and Natthakan Iam-On. "Predicting transitional interval of kidney disease stages 3 to 5 using data mining method." 2016 second Asian conference on defence technology (ACDT). IEEE, 2016. (Year: 2016).*

Norouzi, Jamshid, et al. "Predicting renal failure progression in chronic kidney disease using integrated intelligent fuzzy expert system." Computational and mathematical methods in medicine 2016.1 (2016): 6080814. (Year: 2016).*

Xiao, Jing, et al. "Comparison and development of machine learning tools in the prediction of chronic kidney disease progression." Journal of translational medicine 17 (2019): 1-13. (Year: 2019).*

Perotte, Adler, et al. "Risk prediction for chronic kidney disease progression using heterogeneous electronic health record data and time series analysis." Journal of the American Medical Informatics Association 22.4 (2015): 872-880. (Year: 2015).*

Indian Office Action—Indian Patent Application No. 202317025760 dated May 7, 2026.

Australian Examination Report No. 1 from corresponding Australian Patent Application No. 2021347822, dated Jul. 30, 2026. 4 pages.

* cited by examiner

400

CHRONIC KIDNEY DISEASE (CKD) MACHINE LEARNING PREDICTION SYSTEM, METHODS, AND APPARATUS

PRIORITY CLAIM

This application claims priority to and the benefit as a non-provisional application of U.S. Provisional Patent Application No. 63/082,017, filed Sep. 23, 2020, the entire contents of which are hereby incorporated by reference and relied upon.

BACKGROUND

Chronic kidney disease ("CKD") is a serious and often debilitating medical condition experienced each year by millions of individuals worldwide. An individual with kidney disease has damaged kidneys that are not capable of filtering blood at all, or at least at a sufficient level to remove toxins from the individual's blood. An individual experiencing kidney disease or renal failure can no longer balance water and minerals or excrete daily metabolic load. Toxic end products of nitrogen metabolism (urea, creatinine, uric acid, calcium, phosphorus, sodium, potassium and others) can accumulate in the individual's blood and tissue. Some patients with kidney disease or renal failure may also experience high/low blood pressure and a reduced red blood cell count. Oftentimes, kidney disease is a chronic condition that worsens overtime to the point of complete kidney failure (i.e., end-stage renal disease ("ESRD") or death.

As the world's population improves its overall standard of living, more individuals are able to consume foods and beverages and live lifestyles that lead to CKD. Some studies estimate that as much as 10% of the world's population has some form of CKD. Generally, the global burden of CKD is driven not only by the increasing number of individuals with ESRD, which requires a renal replacement therapy ("RRT"), but also an increasing prevalence of conditions associated with the development of CKD. Currently, individuals receiving RRT consume the majority of healthcare resources for treating CKD. As such, individuals with less severe CKD are often not treated or only marginally treated, which eventually leads to worsening CKD to the point they also eventually need RRT. Efforts are being made by healthcare providers to control predisposition conditions of individuals that are prone to CKD or individuals experiencing an early onset of CKD to delay and/or avoid a progression to ESRD.

Currently, individuals are assessed for CKD by monitoring their estimated glomerular filtration rate ("GFR"), which is indicative as to how much blood passes through an individual's glomeruli (tiny filters in the kidneys) each minute. GFR is typically calculated by a blood creatinine test, taking into account the individual's age, body side, and gender. Generally, a patient having a GFR that is less than 90 mL/minute is considered to have CKD. Proteinuria or albuminuria, a condition characterized by the presence of greater than normal amounts of protein (e.g., albumin) in the urine, may also be indicative of the onset of CKD if the condition persists over three months.

After a patient is assessed with CKD, healthcare providers estimate the patient's potential CKD progression timeline to determine possible treatments. Early detection of CKD is crucial because it allows suitable preventative treatments to be prescribed before any CKD deterioration manifests itself through worsening complications. For instance, a patient with an estimated slow progression may be treated with lifestyle and diet changes in addition to medication. However, a patient with an estimated fast progression may have to receive more intensive clinical treatment, such as starting RRT.

Currently, healthcare providers assess an individual's progression rate through periodic blood creatinine tests and urine analysis. This involves performing blood tests on an individual every few weeks or months, which is burdensome on the healthcare provider and the individual. In some instances, the healthcare provider or the individual does not have the capability to conduct periodic blood tests to assess CKD progression. As a result of these known issues, some individuals may progress faster than initially estimated, where any preventative treatment may be too late or rendered ineffective by the time the individual is assessed again.

A need accordingly exists for a CKD clinician diagnostic tool that provides an accurate prediction of an individual's CKD progression and/or a likeliness that the individual will urgently need to begin dialysis.

SUMMARY

Chronic kidney disease ("CKD") machine learning prediction system, methods, and apparatus are disclosed. The example machine learning prediction system, methods, and apparatus are configured to predict a patient's CKD progression and/or an urgency that a patient will need to start dialysis or RRT in the future. In some embodiments, separate machine learning models are used for projecting CKD progression and estimating a patient's need for urgent-start dialysis.

The disclosed machine learning prediction system, methods, and apparatus provide more information to enable clinicians to make more informed patient care decisions. While knowing a patient's GFR and/or urine albumin-to-creatinine rate/level is useful in determining a current CKD stage of the patient, the data is oftentimes not indicative of a rate of progression through CKD stages or indicative that a patient will urgently need to begin dialysis. Instead, other factors or characteristics may be more indicative as to a rate of CKD progression and/or an urgent need to begin dialysis. The algorithms disclosed herein use machine learning such that classified patient factors/characteristics are modeled and used for determining patient CKD progression predictions and likelihood of urgently needing dialysis. The classified factors/characteristics are readily available from patients' medical records. The factors/characteristics may include gender, race, age, body-mass index ("BMI") blood pressure, creatinine level, GFR, hemoglobin level, and/or albumin level. The factors/characteristics may also include diagnosed causes of CKD including hypertension, diabetes mellitus, obstructive uropathy, glomerulonephritis/autoimmune, polycystic kidney disease, chronic tubulointerstitial nephritis, or chronic pyelonephritis. The factors/characteristics may further include a health history such as hypertension, diabetes, cardiac ischemia, congestive heart failure, or cerebrovascular disease.

In some instances, the disclosed machine learning prediction system, methods, and apparatus are configured to calculate derived factors/characteristics from available patient factors/characteristics. The derived factors/characteristics may include a ratio of factors, such as an albumin-to-creatinine ratio. The derived factors/characteristics may also include a determination of a patient's current or past CKD stage based on their GFR and/or albumin levels.

Together, the factors/characteristics and derived factors/characteristics are associated with positive/negative outcomes related to CKD stage progression, rate of CKD stage progress, and an urgent need to start dialysis for a population of patients with known CKD outcomes. The associations are used to determine probabilities or likelihoods that patients with similar factors/characteristics will have similar outcomes.

As disclosed herein, the machine learning prediction system, methods, and apparatus compare characteristics of a patient under analysis to classified factors/characteristics of known patients that are represented in predictive algorithms/models. The probabilities of the classified factors/characteristics that compare favorably with the characteristics of the patient under analysis are reported as predicted CKD outcomes. Clinicians may use the reported CKD outcomes for treatment planning purposes to slow CKD progression and/or to determine a need for urgent dialysis.

In some embodiments, the disclosed machine learning prediction system, methods, and apparatus comprise a CKD progression projection algorithm or model. As disclosed herein, the CKD progression projection algorithm or model is configured to provide a likelihood or probability that a patient may progress to a next stage of CKD within a designated timeframe. In some embodiments, the CKD progression algorithm or model includes an ensemble machine learning algorithm configured to determine a likeliness that a patient will transition to a new CKD stage and a length of time it may take the patient to transition to the new CKD stage. The model or algorithm is configured to compare a patient's physiological data, demographic data, medical history, and other identified characteristics/factors to modeled classifiers that were trained using known patient CKD progression data. Based on the comparison, the model determines a closest matching prediction decile and outputs the percentage and timeframe for that decile. In some alternative embodiments, the CKD progression model may take an average or weighted average of a patient's comparison to one or more deciles for estimating a CKD stage progression likelihood and timeframe.

Additionally or alternatively, the disclosed machine learning prediction system, methods, and apparatus comprise a CKD urgent-start dialysis projection algorithm or model. As disclosed herein, the CKD progression urgent-start dialysis projection algorithm or model is configured to provide a likelihood or probability that a patient may need dialysis within a designated timeframe. The model or algorithm is configured to compare a patient's physiological data, demographic data, medical history, and other identified characteristics/factors to modeled classifiers that were trained using known patient CKD urgent-start dialysis data. Based on the comparison, the model or algorithm determines a closest matching prediction decile and outputs the percentage and timeframe for that decile. In some alternative embodiments, the CKD urgent-start dialysis model may take an average or weighted average of a patient's comparison to one or more deciles for estimating a likelihood that a patient will need to begin dialysis within certain discrete timeframes.

The disclosed machine learning prediction system, methods, and apparatus of the present disclosure are applicable, for example, to fluid delivery for plasmapheresis, hemodialysis ("HD"), hemofiltration ("HF") hemodiafiltration ("HDF"), and continuous renal replacement therapy ("CRRT") treatments. The disclosed machine learning prediction system, methods, and apparatus described herein are also applicable to peritoneal dialysis ("PD"), intravenous drug delivery, and nutritional fluid delivery. These modalities may be referred to herein collectively or generally individually as medical fluid delivery or treatment.

As described in detail below, the CKD machine learning prediction system, methods, and apparatus of the present disclosure may operate within an encompassing medical platform that may include many machines comprising many different types of devices, patients, clinicians, doctors, service personnel, electronic medical records ("EMR") databases, websites, resource planning systems, and business intelligence. The CKD machine learning prediction system, methods, and apparatus of the present disclosure are configured to operate seamlessly within the overall system and without contravening its rules and protocols.

In light of the disclosure herein and without limiting the disclosure in any way, in a first aspect of the present disclosure, which may be combined with any other aspect listed herein unless specified otherwise, a system for estimating a patient's chronic kidney disease ("CKD") progression includes a memory device storing patient characteristic data for a patient undergoing analysis, the patient characteristic data including demographic/physiological data, a CKD entry stage, a diagnosed cause of CKD, and a health history. The system also includes an ensemble machine learning algorithm configured to predict a progression to a next stage of CKD and a timeframe of the progression of the next stage of CKD, the ensemble machine learning algorithm containing prediction decile classifiers that each includes percentages of known patients that progressed from one moderate CKD stage to a next moderate or severe CKD stage for discrete timeframes. The system further includes an analytics processor communicatively coupled to the memory device. The analytics processor in conjunction with the ensemble machine learning algorithm are configured to classify the patient undergoing analysis into a closest matching prediction decile for the CKD entry stage of the patient by comparing the patient characteristic data of the patient under analysis to classifications of patient characteristic data provided in the ensemble machine learning algorithm, determine a probability that the patient undergoing analysis will progress to a next moderate or severe CKD stage for each of the discrete timeframes based on the closest matching prediction decile, and display, via a user interface, the percentage likelihoods that the patient undergoing analysis will progress to the next moderate or severe CKD stage for the discrete timeframes.

In accordance with a second aspect of the present disclosure, which may be used in combination with any other aspect listed herein unless stated otherwise, the demographic/physiological data includes at least one of a gender, a race, an age, a body-mass index, a blood pressure, a creatinine level, a glomerular filtration rate ("GFR"), a hemoglobin level, or an albumin level.

In accordance with a third aspect of the present disclosure, which may be used in combination with any other aspect listed herein unless stated otherwise, the diagnosed cause of CKD includes at least one of hypertension, diabetes mellitus, obstructive uropathy, glomerulonephritis/autoimmune, polycystic kidney disease, chronic tubulointerstitial nephritis, or chronic pyelonephritis.

In accordance with a fourth aspect of the present disclosure, which may be used in combination with any other aspect listed herein unless stated otherwise, the health history includes at least one of hypertension, diabetes, cardiac ischemia, congestive heart failure, or cerebrovascular disease.

In accordance with a fifth aspect of the present disclosure, which may be used in combination with any other aspect listed herein unless stated otherwise, the percentages of known patients that progressed from one moderate CKD stage to a next moderate or severe CKD stage is determined using patient population data including patient characteristic data, known CKD progression data, and exit results.

In accordance with a sixth aspect of the present disclosure, which may be used in combination with any other aspect listed herein unless stated otherwise, the exit results include at least one of a dialysis therapy, a renal replacement therapy ("RRT"), death, kidney transplant, or palliative care.

In accordance with a seventh aspect of the present disclosure, which may be used in combination with any other aspect listed herein unless stated otherwise, the known CKD progression data identifies stage progressions based on a change of an estimated glomerular filtration rate ("GFR") that is associated with a different moderate or severe CKD stage, or at least a 25% change of the estimated GFR from a previously known GFR.

In accordance with an eighth aspect of the present disclosure, which may be used in combination with any other aspect listed herein unless stated otherwise, the CKD entry stage of the patient is based on at least one of an estimated GFR of the patient or a length of time the patient has been experiencing proteinuria.

In accordance with a ninth aspect of the present disclosure, which may be used in combination with any other aspect listed herein unless stated otherwise, the discrete timeframes include at least one of 30 days, 60 days, 90 days, 120 days, 180 days, and 360 days.

In accordance with a tenth aspect of the present disclosure, which may be used in combination with any other aspect listed herein unless stated otherwise, the moderate or severe CKD stages include Stage 3A with a GFR between 45 to 59 mL/min, Stage 3B with a GFR between 30 to 44 mL/min, Stage 4 with a GFR between 15 to 29 mL/min, and Stage 5 with a GFR less than 15 mL/min.

In accordance with an eleventh aspect of the present disclosure, which may be used in combination with any other aspect listed herein unless stated otherwise, the ensemble machine learning algorithm includes prediction decile classifiers that each include percentages of known patients that progressed from one minor CKD stage to a next moderate or severe CKD stage for discrete timeframes, and the CKD entry stage includes at least one of Stage 1 with a GFR greater than 90 mL/min, Stage 2 with a GFR between 60 and 89 mL/min, Stage 3A with a GFR between 45 to 59 mL/min, Stage 3B with a GFR between 30 to 44 mL/min, or Stage 4 with a GFR between 15 to 29 mL/min.

In accordance with a twelfth aspect of the present disclosure, which may be used in combination with any other aspect listed herein unless stated otherwise, the user interface is displayed on a clinician computer.

In accordance with a thirteenth aspect of the present disclosure, which may be used in combination with any other aspect listed herein unless stated otherwise, a system for estimating a likelihood a patient with chronic kidney disease ("CKD") will need urgent start dialysis includes a memory device storing patient characteristic data for a patient undergoing analysis, the patient characteristic data including demographic/physiological data, a CKD entry stage, a diagnosed cause of CKD, and a health history. The system also includes a machine learning algorithm configured to predict a likelihood the patient undergoing analysis will need an urgent start of dialysis, the machine learning algorithm containing prediction decile classifiers that each includes percentages of known patients that needed an urgent start of dialysis for discrete timeframes. The system further includes an analytics processor communicatively coupled to the memory device. The analytics processor in conjunction with the ensemble machine learning algorithm are configured to classify the patient undergoing analysis into a closest matching prediction group for the CKD entry stage of the patient by comparing the patient characteristic data of the patient under analysis to classifications of patient characteristic data provided in the machine learning algorithm, determine probabilities that the patient undergoing analysis will need an urgent start of dialysis for the discrete timeframes based on the closest matching prediction decile, and display, via a user interface, the percentage likelihoods that the patient undergoing analysis will need the urgent start of dialysis for the discrete timeframes.

In accordance with a fourteenth aspect of the present disclosure, which may be used in combination with any other aspect listed herein unless stated otherwise, the demographic/physiological data includes at least one of a gender, a race, an age, a body-mass index, a blood pressure, a creatinine level, a glomerular filtration rate ("GFR"), a hemoglobin level, or an albumin level.

In accordance with a fifteenth aspect of the present disclosure, which may be used in combination with any other aspect listed herein unless stated otherwise, the diagnosed cause of CKD includes at least one of hypertension, diabetes mellitus, obstructive uropathy, glomerulonephritis/autoimmune, polycystic kidney disease, chronic tubulointerstitial nephritis, or chronic pyelonephritis.

In accordance with a sixteenth aspect of the present disclosure, which may be used in combination with any other aspect listed herein unless stated otherwise, the health history includes at least one of hypertension, diabetes, cardiac ischemia, congestive heart failure, or cerebrovascular disease.

In accordance with a seventeenth aspect of the present disclosure, which may be used in combination with any other aspect listed herein unless stated otherwise, the percentages of known patients that progressed from one CKD stage to a next CKD stage was determined using patient population data including patient characteristic data, known CKD progression data, and exit results.

In accordance with an eighteenth aspect of the present disclosure, which may be used in combination with any other aspect listed herein unless stated otherwise, the CKD stages include Stage 1 with a GFR greater than 90 mL/min, Stage 2 with a GFR between 60 and 89 mL/min, Stage 3A with a GFR between 45 to 59 mL/min, Stage 3B with a GFR between 30 to 44 mL/min, Stage 4 with a GFR between 15 to 29 mL/min, and Stage 5 with a GFR less than 15 mL/min.

In accordance with a nineteenth aspect of the present disclosure, which may be used in combination with any other aspect listed herein unless stated otherwise, the analytics processor is configured to receive an indication to start a dialysis treatment, and cause a dialysis treatment to be prepared for the patient.

In accordance with a twentieth aspect of the present disclosure, which may be used in combination with any other aspect listed herein unless stated otherwise, the system further includes a dialysis machine configured to perform the dialysis treatment for the patient.

In a twenty-first aspect of the present disclosure, any of the structure and functionality disclosed in connection with FIGS. 1 to 8 may be combined with any other structure and functionality disclosed in connection with FIGS. 1 to 8.

In light of the present disclosure and the above aspects, it is therefore an advantage of the present disclosure to provide a CKD machine learning algorithm that is configured to provide a prediction regarding a patient's CKD progression over time.

It is another advantage of the present disclosure to provide a CKD machine learning algorithm that is configured to provide a prediction regarding a patient's need to urgently start dialysis or other RRT.

It is a further advantage of the present disclosure to provide, to a clinician or other healthcare provider for clinician diagnosis and treatment, information that is indicative of a projection of a patient's CKD progression over time and/or a patient's need to urgently start dialysis.

It is still a further advantage of the present disclosure to provide improved patient outcomes from the onset of detection of CKD to slow disease progression.

Additional features and advantages are described in, and will be apparent from, the following Detailed Description and the Figures. The features and advantages described herein are not all-inclusive and, in particular, many additional features and advantages will be apparent to one of ordinary skill in the art in view of the figures and description. Also, any particular embodiment does not have to have all of the advantages listed herein and it is expressly contemplated to claim individual advantageous embodiments separately. Moreover, it should be noted that the language used in the specification has been selected principally for readability and instructional purposes, and not to limit the scope of the inventive subject matter.

DETAILED DESCRIPTION

Figure 1:
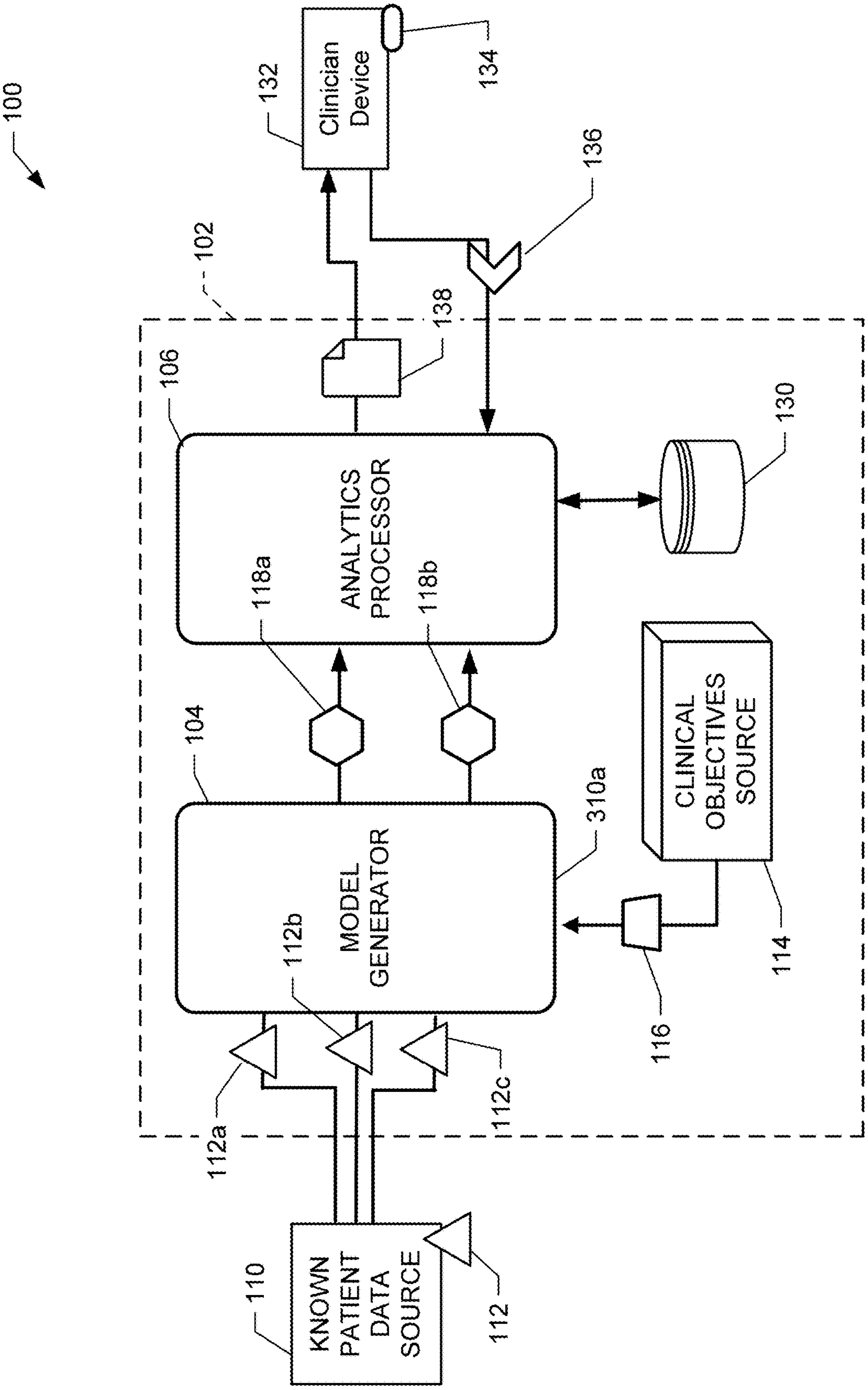
FIG. 1 is a diagram of a CKD machine learning predictive system including a model generator and an analysis processor, according to an example embodiment of the present disclosure.

CKD machine learning prediction system, methods, and apparatus are disclosed herein. The example CKD machine learning prediction system, methods, and apparatus are configured to provide a projection as to whether a patient may progress to a next stage of CKD and/or whether the patient may need to urgently start dialysis. The machine learning algorithms disclosed herein include dynamic, multifactorial predictive algorithms that are programmed to consider clinical, pharmacological, and extra-clinical factors that adversely impact kidney function. The predictions provided by the machine learning system, methods, and apparatus convey information to clinicians for improving CKD treatment before the disease worsens. In some instances, the predictions may be used for selecting a treatment plan, a dialysis treatment, and/or RRT.

Reference is made herein to machine learning algorithms and models, where the terms are used interchangeably. As disclosed, the machine learning algorithms and models are configured to receive certain patient factors/characteristics, which are processed and compared to classified factors/characteristics for determining a probability or likelihood of a positive result. The algorithms or models are defined by one or more machine-readable instructions stored in a memory device. The algorithms and models are also defined by factor/characterization tuning parameters/weights/correlation indices that are created during creation of the algorithms or models. The tuning parameters/weights/correlation indices are also stored in a memory device. Execution of the one or more machine-readable instructions by a processor causes operations to be performed using the stored tuning parameters/weights/correlation indices. These operations enable analysis of patient characteristics of a designated patient to be processed through the example machine learning algorithms and models for providing a predicted outcome.

Reference is also made to machine learning model deciles of positive outcomes. As disclosed herein, the machine learning models/algorithms classify/order known patients into ten groups for each CKD stage. The models/algorithms determine probabilities of a positive outcome for CKD progression and/or CKD urgent-start dialysis for each decile of each CKD stage. The probabilities are determined for a range of discrete timeframes, such as having a positive result within 30 days, 60 days, 90 days, 120 days, 180 days, 360 days, etc. for that decile of the CKD stage. In other examples, different ranges/classifications may be used. For example, classifications may be made in a non-uniform manner based on natural delineations between known patient characteristics/factors. For example, deciles 8 to 10 disclosed herein may be partitioned into further groups for greater resolution where there is more outcome variability compared to deciles 1 to 5, which could be combined into a single group given the general outcome homogeneity for known patient outcomes.

As provided herein, the example system, methods, and apparatus provide more accurate predictions compared to known clinical methods for treating CKD. For instance, the Kidney Disease: Improving Global Outcomes ("KDIGO") organization recommends classifying CKD according to the underlying etiology and by the level of albuminuria in patients. This definition and classification is generally accepted and implemented worldwide despite known limitations in the current equations used to calculate a patient's glomerular filtration rate ("GFR") from serum creatinine, which could result in overestimation, particularly among patients with a GFR greater than 60 mL/minute ("min"). Current clinical practice includes assessing a patient's progression of CKD through periodic estimation of the patient's GFR, which is based on an assumption of predictable longitudinal decline. Recent studies, however, have shown that certain acute events, medications, and sudden changes in blood pressure can lead to variation in the patient's GFR trajectory, and thus undermine the presumed rate of kidney function decline.

The example system, methods, and apparatus disclosed herein provide a unique assessment of factors that contribute to CKD progression and the conditions that could influence the trajectory of GFR decline in patients. Reference is made herein to stages of CKD. Table 1 below shows KDIGO's definitions of the different stages of CKD, which are based on a patient's estimated GFR and a length of time a patient is experiencing proteinuria. A rapid progression of CKD is defined as an absolute annual decline of GFR≥5 ml/min in each year with at last GFR<90 ml/min.

TABLE 1

Stages of CKD

| Stage | Definition |
|---|---|
| Stage 1 | Normal or high GFR (GFR >90 mL/min) and persistent (≥3 months) proteinuria |
| Stage 2 | Mild CKD (GFR = 60-89 mL/min) and persistent (≥3 months) proteinuria |
| Stage 3A Moderate CKD | (GFR = 45-59 mL/min) |
| Stage 3B Moderate CKD | (GFR = 30-44 mL/min) |
| Stage 4 Severe CKD | (GFR = 15-29 mL/min) |
| Stage 5 End Stage CKD | (GFR <15 mL/min) CKD stage 5 requiring dialysis or transplant for survival is also known as end-stage renal disease (ESRD) |
| Stage 5D | ESRD in dialysis |

The example predictive CKD machine learning algorithms disclosed herein are configured to assess a patient's likelihood of progressing from a current CKD stage to a next CKD stage. As such, the predictive CKD machine learning algorithms provide an assessment of progression between each of the stages shown in Table 1. In some embodiments, the predictive CKD machine learning algorithms may provide assessments only for moderate or severe Stages 3A to 5 or 5D. In addition to determining if a patient will progress to a next CKD stage, the predictive CKD machine learning algorithms are configured to determine a rate or a timeframe of the progression. In some instances, the rate may be defined as a likelihood of progression within a discrete timeframe, such as 30 days, 60 days, 90 days, 120 days, 180 days, and/or 360 days. The predictive CKD machine learning algorithms disclosed herein may also provide an assessment of a patient's risk of urgent-start dialysis, which refers to the urgent initiation of dialysis for ESRD patients with no pre-established functional vascular access or peritoneal dialysis ("PD") catheter. As disclosed herein, the progression likelihood and rate may be combined into an ensemble machine learning algorithm (e.g., a CKD Stage Progression Prediction Model), while the urgent-start dialysis risk is determined by a second machine learning algorithm (e.g., a CKD Urgent-start Dialysis Prediction Model).

I. CKD MACHINE LEARNING PREDICTIVE SYSTEM

FIG. 1 is a diagram of a CKD machine learning predictive system 100, according to an example embodiment of the present disclosure. The example system 100 includes a CKD management server 102, which is configured to create/update the predictive machine learning algorithms disclosed herein and provide patient predictions using the algorithms. The CKD management server 102 includes a model generator 104 configured to generate the predictive machine learning algorithms disclosed herein. The CKD management server 102 also includes an analytics processor 106 configured to apply patient characteristic data for a patient under analysis to the one or more predictive machine learning algorithms to assess or predict the patient's CKD progression probably, progression rate, and probably of needing urgent-start dialysis. While shown as both being part of the CKD management server 102, in other embodiments, the model generator 104 may be separate from the analytics processor 106. For example, the model generator 104 may be provided at a back-end server while the analytics processor 106 is provisioned as a cloud-based service that is available to clinician devices.

It should be appreciated that the operations described in connection with the model generator 104 and the analytics processor 106 may be implemented using one or more computer programs or components. The programs of the components may be provided as a series of computer instructions on any computer-readable medium, including random access memory ("RAM"), read only memory ("ROM"), flash memory, magnetic or optical disks, optical memory, or other storage media. The instructions may be configured to be executed by a processor of the management server 102, which when executing the series of computer instructions performs or facilitates the performance of all or part of the disclosed methods and procedures.

As shown in FIG. 1, the model generator 104 is communicatively coupled to a known patient data source 110, which may include a memory device storing known patient characteristic data 112 for modeling. The model generator 104 partitions received characteristic data into training data **112*a* for training and/or creating the predictive machine learning algorithms disclosed herein. The model generator 104 also partitions the received characteristic data 112 into test data 112*b* for testing an accuracy of the predictive machine learning algorithms disclosed herein. The received data 112 is further partitioned into validation data 112*c*** for validating the predictive machine learning algorithms disclosed herein.

The model generator 104 is also communicatively coupled to a clinical objectives source 114, which may include a memory device storing clinical objectives of for the models. In some embodiments, the clinical objectives source 114 may include a translation of clinical objectives into machine learning objectives 116. The model generator 104 uses the machine learning objectives 116 and the training data **112*a* to create one or more predictive machine learning algorithms, shown as CKD stage progression prediction model 118*a* and CKD urgent-start dialysis prediction model 118*b*. In the illustrated embodiment, the machine learning objectives 118 includes a first objective to provide a CKD stage progression probability or likelihood, a second objective to provide a rate of CKD progression, and a third objective to provide a probability or likelihood that urgent-start dialysis will be needed within a defined timeframe. The CKD stage progression prediction model 118*a* achieves the progression and rate objectives as an ensemble model. The CKD urgent-start dialysis prediction model 118*b* achieves the urgent-start dialysis objective. In some embodiments, the model generator 104** tests different combinations of objectives and models to identify a most optimal approach for achieving the specified objections.

Figure 2:
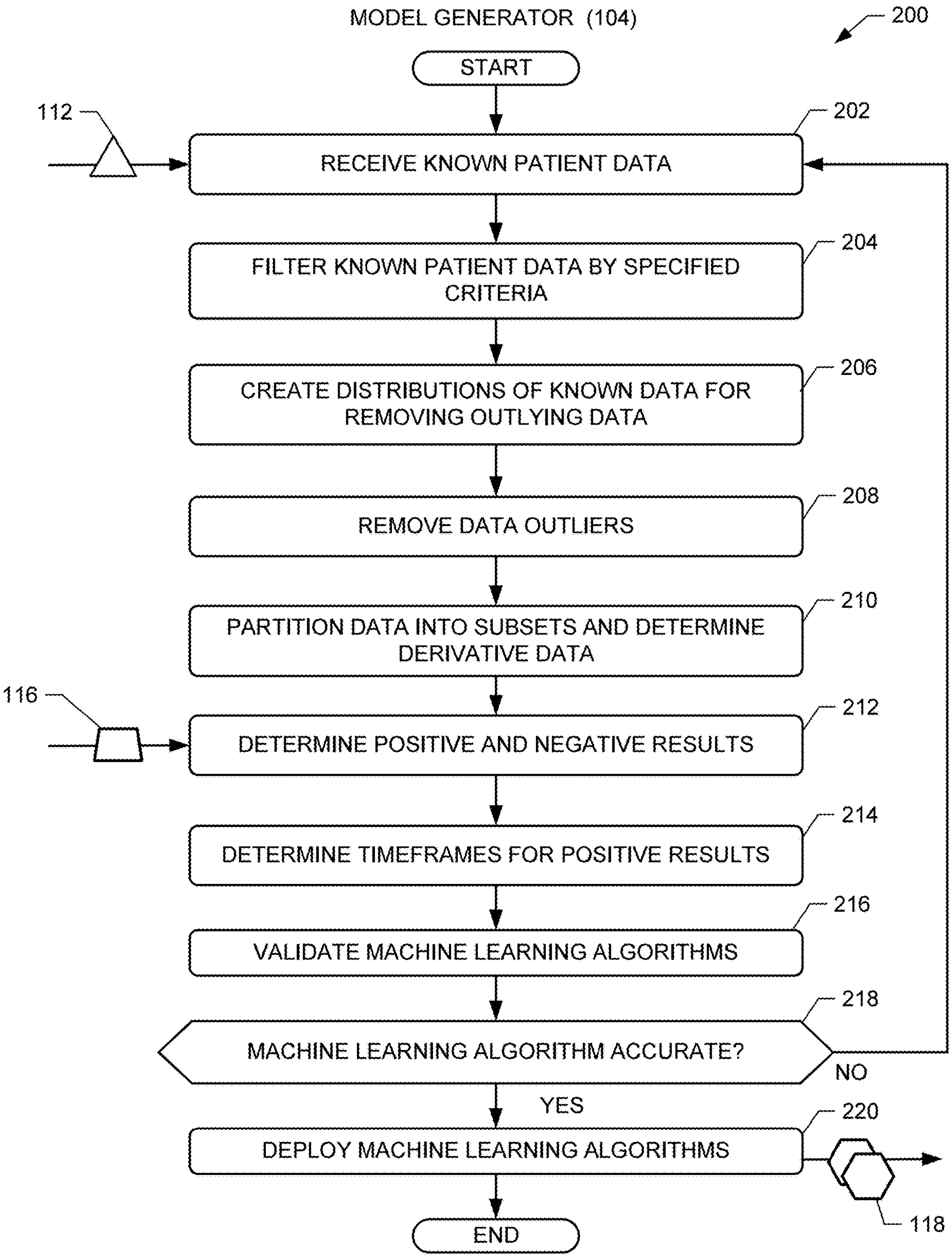
FIG. 2 is a flow diagram of an example procedure to create CKD predictive machine learning algorithms disclosed herein, according to an example embodiment of the present disclosure.

FIG. 2 is a flow diagram of an example procedure 200 to create the CKD predictive machine learning algorithms disclosed herein, according to an example embodiment of the present disclosure. Although the procedure 200 is described with reference to the flow diagram illustrated in FIG. 2, it should be appreciated that many other methods of performing the steps associated with the procedure 200 may be used. For example, the order of many of the blocks may be changed, certain blocks may be combined with other blocks, and many of the blocks described may be optional. In an embodiment, the number of blocks may be changed based data preprocessing and filtering and/or the types of machine learning models being developed. The actions described in the procedure 200 are specified by one or more instructions that are stored in a memory device, and may be performed among multiple devices including, for example the model generator 104.

The example procedure 200 begins when the model generator 104 receives known patient characteristic data 112 from, for example, a known patient data source 110 (block 202). The known patient data source 110 may include one or more electronic medical records ("EMR") databases that are located at clinics or hospitals and store electronic information concerning patients. Table 2 below shows an example of the known patient characteristic data 112 received by the model generator 104. In the illustrated example, data for 7,131 patients was received and used for creating the CKD machine learning models disclosed herein. The known patient data may include GFR, creatinine level, hemoglobin level, and/or albumin level for each patient, which may be determined or estimated from patient blood tests. The known patient data may also include blood pressure, body temperature, etc.

TABLE 2

| Known Patient Data | |
|---|---|
| Factors/Characteristics | Number (%) of Patients n = 7,131 |
| **Gender** | |
| Female | 3,599 (50.5) |
| Male | 3,532 (49.5) |
| **Race** | |
| White or Mestizo | 6,828 (95.8) |
| African-American | 292 (4.1) |
| Indigene | 11 (0.2) |
| **Age** | |
| Mean (SD), in years | 64.8 (11.0) |
| **Clinic visits** | |
| Count (SD), per patient | 15.6 (10.3) |
| **CKD Stage upon entry to the study** | |
| 3A | 3,413 (47.9) |
| 3B | 2,262 (31.7) |
| 4 | 1,456 (20.4) |
| **Documented cause of CKD** | |
| Hypertension | 3,063 (43.0) |
| Diabetes Mellitus | 1,712 (24.0) |
| Obstructive Uropathy | 411 (5.8) |
| Glomerulonephritis/Autoimmune | 311 (4.4) |
| Polycystic Kidney Disease | 89 (1.2) |
| Chronic tubulointerstitial nephritis | 49 (0.7) |
| Chronic pyelonephritis | 10 (0.1) |
| Other | 706 (9.9) |
| Unknown | 780 (10.9) |
| **Health History** | |
| Hypertension | 6,067 (85.1) |
| Diabetes | 2,444 (34.3) |
| Cardiac ischemia | 736 (10.3) |
| Congestive Heart Failure | 376 (5.3) |
| Cerebrovascular Disease | 142 (2.0) |
| **BMI** | |

TABLE 2-continued

| Known Patient Data | |
|---|---|
| Factors/Characteristics | Number (%) of Patients n = 7,131 |
| <18.5 (underweight) | 120 (1.7) |
| 18.5-24.9 (normal) | 2,583 (36.2) |
| 25.0-29.9 (overweight) | 3,028 (42.5) |
| ≥30.0 (obese) | 1,400 (19.6) |
| **Cause of exit from the study** | |
| End of the study | 3,066 (43.0) |
| Change of provider or loss of insurance | 2,201 (30.9) |
| Consultation nephology | 613 (8.6) |
| Dialysis therapy | 577 (8.1) |
| Suspension or abandonment | 406 (5.7) |
| Death | 255 (3.6) |
| Status Post Kidney Transplantation | 12 (0.2) |
| Palliative care | 1 (0.0) |

Figure 3:
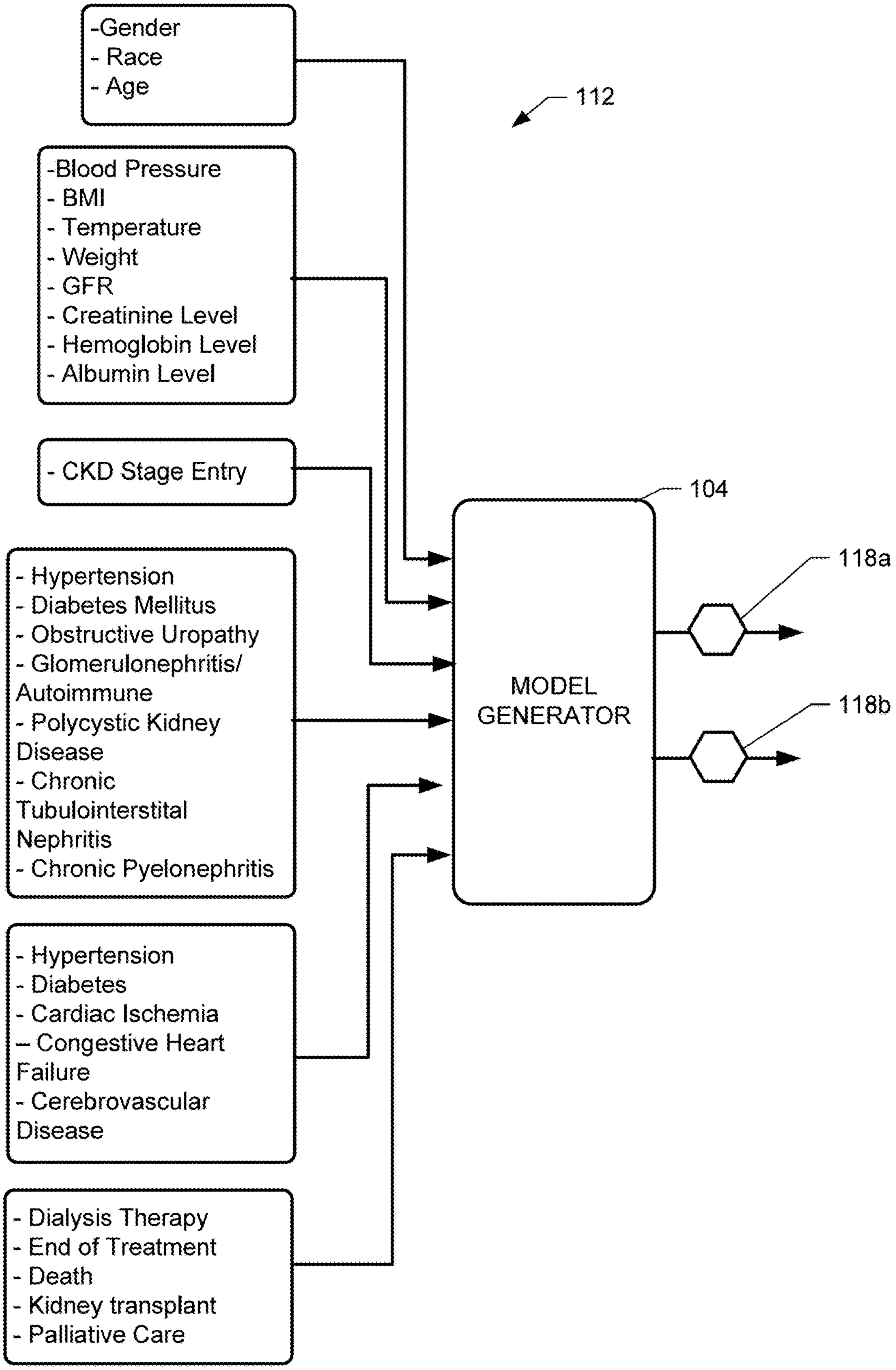
FIG. 3 is a diagram of example patient characteristic data received by the model generator of FIG. 1, according to an example embodiment of the present disclosure.

FIG. 3 is a diagram of example patient characteristic data 112 received by the model generator 104, according to an example embodiment of the present disclosure. The patient characteristic data 112 may include demographic data such as age, gender, and race. The patient characteristic data 112 may also include physiological data, such as blood pressure, BMI, temperature, weight, GFR, creatinine levels, hemoglobin levels, and albumin levels. In some instances, the patient characteristic data 112 may include a CKD stage entry. Otherwise, the model generator 104 may determine a patient's CKD stage from the GFR and/or albumin data. The patient characteristic data 112 may further include a diagnosed cause of CKD including hypertension, diabetes mellitus, obstructive uropathy, glomerulonephritis/autoimmune, polycystic kidney disease, chronic tubulointerstitial nephritis, or chronic pyelonephritis. Moreover, the patient characteristic data 112 may include health history such as hypertension, diabetes, cardiac ischemia, congestive heart failure, or cerebrovascular disease. FIG. 3 also shows that the patient characteristic data 112 may include an end known result for the patients including, dialysis treatment or RRT, end of treatment, death, kidney transplant, and palliative care. It should be appreciated that less or additional patient characteristic data 112 may be used by the model generator 104.

The above-known patient characteristic data 112 represents patients at different stages of CKD in which the patients received medical care and periodic monitoring. The characteristic data 112 includes timestamps provided for clinical activities including vital sign measurements, laboratory values, pharmacological interventions, hospitalizations for urgent-start dialysis, appointment dates, and procedures (including hemodialysis and peritoneal dialysis).

Returning to FIG. 2, after receiving the data, the model generator 104 is configured to filter the characteristic data 112 by specified criteria (block 204). For example, the model generator 104 may only retain data for patients between 18 and 80 years of age at a time of first treatment for CKD, patients that reached Stage 3 or 4 CKD, and/or patients for which at least three months, six months, one year, or two years of data is available. In some embodiments, the model generator 104 may filter patient characteristic data 112 for patients that reached Stage 5 CKD (ESRD) and had at least three months of follow-up and dialysis treatment. Further, the model generator 104 may filter patient characteristic data 112 for patients that have at least three separate GFR measurements.

After filtering, the model generator 104 is configured to create data distributions of the filtered data 112 (block 206). Distributions of the characteristic data 112, such as GFR, blood pressure, weight, BMI, creatinine level, hemoglobin level, and/or albumin level are created, examined, and compared to normal or expected behavior for a variable of that type (clinical or administrative). The comparison may reveal data errors, missing data, and other abnormally behaving data that is to be addressed before modeling. The model generator 104 may remove patients that have data outside of a normal distribution (block 208). Further, the model generator 104 may provide for missing data using timestamped medical records from which the characteristic data 112 was received. The model generator 104 may also analyze the structure and aggregations of the characteristic data 112 by identifying variable formats, the nature of the variables, and data dependencies among the variables. For example, the model generator 104 may determine that an albumin-to-creatinine ratio is useful for patient classification for CKD progression. Further, the model generator 104 may determine a CKD stage (including a CKD entry stage) for a patient based on GFR and/or an albumin level.

As shown in FIG. 2, the model generator 104 partitions the processed patient characteristic data 112 into different subsets (block 210). For example, subsets are included for training data, validation data, and test data, where a patient (and their corresponding data) is assigned to one of the three subsets. The model generator 104 also determines derivative data (e.g., engineered variables) from the patient characteristic data 112. The derivate data may include calculating ratios between certain data, such as albumin-to-creatinine ratio. The derivative data may also include a determination of a patient's CKD stage at a point in time based on a GFR and/or albumin level.

The model generator 104 next correlates positive and negative results with the distribution of training data (e.g., data 112*a*) (block 212). The classification of positive and negative results is based on the machine learning objectives 116. For CKD stage progression, the positive results comprise characteristic data 112 that corresponds to progression from one CKD stage to the next CKD stage. The model generator 104 creates classifications for each of the CKD stages. In some instances, the model generator 104 may create classifications from Stage 3A or Stage 3B to Stage 5. The model generator 104 identifies positive results for a stage progression based on the GFR alone and/or when a known patient's GFR changed at least 25% from a prior GFR measurement.

For CKD stage rate, the model generator 104 may create and/or use patient trajectory charts (from the characteristic data 112) that consider a change in GFR over time. Positive outcomes are determined based on rates between known CKD stage progressions, which are determined based on GFR measurements, discussed above. For urgent-start dialysis outcomes, the positive results are based on indicates of patient starting a dialysis treatment.

For the positive results, the model generator 104 also determines timeframes for each of the positive results (block 214). This includes, for each patient, sampling patient data at a point in time during their medical history. The sampled patient data up until the sampled point is entered into the machine learning algorithm to generate a prediction. If the patient experienced a positive result, the model generator 104 calculates a timeframe based on the generated prediction and the positive result. The model generator 104 creates classifications of the timeframes for combining the patient data for calculating probabilities of the positive result for each of the timeframes. In some examples, the discrete timeframes include 30 days, 60 days, 90 days, 120 days, 180 days, and 360 days.

In an example, a known Patient A is sampled at a certain date that corresponds to a point in the middle of their treatment. The patient data of Patient A up to the certain date is analyzed through the machine learning algorithms to determine, for example, a predicted probability for progressing from Stage 3B to Stage 4 CKD. The algorithm may provide an estimation of 45 days. The model generator 104 compares the prediction to the actual known result of Patient A, which in this example the progression from Stage 3B to Stage 4 CKD occurred at 60 days. In this example, the model generator 104 refines the machine learning algorithm based on the difference between the predicted 45 days and the actual 60 days. Thus, for a timeframe of at least 60 days, Patient A had a positive progression from Stage 3B to Stage 4 CKD of 100% and 0% before the 60 day timeframe. Patient A's probabilities are combined with other patients to provide estimates for the entire training data set over the different timeframes.

In some instances, the model generator 104 resamples the training patient data 112*a* multiple times to refine the machine learning models. For example, for Patient A, the patient may be sampled at a first date/time, a second subsequent date/time, and a third/date time for refining the machine learning algorithms. After the models and/or algorithms are created and/or refined, the model generator 104 is configured to perform a validation using a subset 112*b* of the patient characteristic data 112 that was separated from the training data 112*a* (block 216). The model generator 104 is configured to generate predictions using the validated data, then compare the predictions to the actual known outcomes to determine a statistical accuracy. The statistics may include a positive predictive value, factor/characteristic sensitivity, F1-score, and/or area under a receiver operating characteristic ("ROC") curve.

The model generator 104 determines if the machine learning algorithms are accurate by analyzing the statistics (block 218). If the algorithms are not accurate to within a defined accuracy (e.g., 95% accurate), the example procedure 200 returns to block 202 to refine the algorithms or create new machine learning algorithms using the same and/or different known patent characteristic data 112. However, if the machine learning algorithms are accurate, the model generator 104 deploys the machine learning algorithms 118 (block 220). This may include providing the CKD stage progression prediction model 118*a* (e.g., a first machine learning algorithm) and/or the CKD urgent-start dialysis prediction model 118*b* (e.g., a first machine learning algorithm) to the analytics processor 106. The example procedure 200 then ends. It should be appreciated that in some instances, the model generator 104 may update the machine learning algorithms as new training data becomes available.

II. CKD STAGE PROGRESSION PREDICTION MODEL EMBODIMENT

This section discusses the properties and accuracy of the CKD stage progression prediction model 118*a*. As shown in Tables 3 and 4 below, the example model 118*a* demonstrates discriminative performance in identifying a risk of progression over different discrete timeframes (corresponding to potential clinical follow-up periods), as illustrated by the positive predictive value, sensitivity, F1-score, and area under the ROC curve.

TABLE 3

CKD Stage Progression Prediction Model - Machine Learning Metrics

| Timeframe (days) | Prevalence | Positive Predictive Value | Sensitivity | F1-score | AUC |
|---|---|---|---|---|---|
| 30 | 4.3% | 0.19 | 0.41 | 0.26 | 0.84 |
| 60 | 13.8% | 0.59 | 0.64 | 0.62 | 0.89 |
| 90 | 21.2% | 0.65 | 0.66 | 0.66 | 0.88 |
| 120 | 29.2% | 0.69 | 0.70 | 0.69 | 0.87 |
| 180 | 33.5% | 0.72 | 0.72 | 0.72 | 0.86 |
| 360 | 37.2% | 0.69 | 0.79 | 0.74 | 0.86 |

Timeframe refers to number of days from prediction within which the positive outcome occurred
Prevalence is the percent of samples with positive outcomes (i.e. stage change)
AUC—area under the curve; AUCs of 0.50 = chance level discriminative accuracy; 1.0 = perfect discriminative accuracy.

As shown in Table 4, the model output is grouped by decile (as averages of the different CKD stages) to illustrate discrimination of patients with higher probability of progression from one CKD stage to another and to make the model more actionable. Close examination of the decile analysis for the stage progression prediction model shows that the model is able to segment patients across the entire range of risk. For example, as the decile increases, the percent of patients with stage progression also increases. The higher deciles not only tended to have higher stage progression rates, but they also tended to have more rapid stage progression.

TABLE 4

CKD Stage Progression Prediction Model - Percent with Positive Outcomes

| | Timeframe | | | | | |
|---|---|---|---|---|---|---|
| Prediction Decile | 30 days | 60 days | 90 days | 120 days | 180 days | 360 days |
| 1 | 0.0% | 0.0% | 1.9% | 1.9% | 2.8% | 5.6% |
| 2 | 0.0% | 0.9% | 0.9% | 1.8% | 4.6% | 4.6% |
| 3 | 0.9% | 1.8% | 4.6% | 6.5% | 10.3% | 15.0% |
| 4 | 0.9% | 2.8% | 5.6% | 14.9% | 16.8% | 19.6% |
| 5 | 0.0% | 3.8% | 3.8% | 12.3% | 15.1% | 17.0% |
| 6 | 2.8% | 6.6% | 14.1% | 22.6% | 25.4% | 26.3% |
| 7 | 0.9% | 8.4% | 16.8% | 27.1% | 32.7% | 44.8% |
| 8 | 7.5% | 13.2% | 31.1% | 50.0% | 58.5% | 62.3% |
| 9 | 12.3% | 33.1% | 49.1% | 67.0% | 75.5% | 82.1% |
| 10 | 17.8% | 67.3% | 84.1% | 87.8% | 92.5% | 94.4% |

Figure 4:
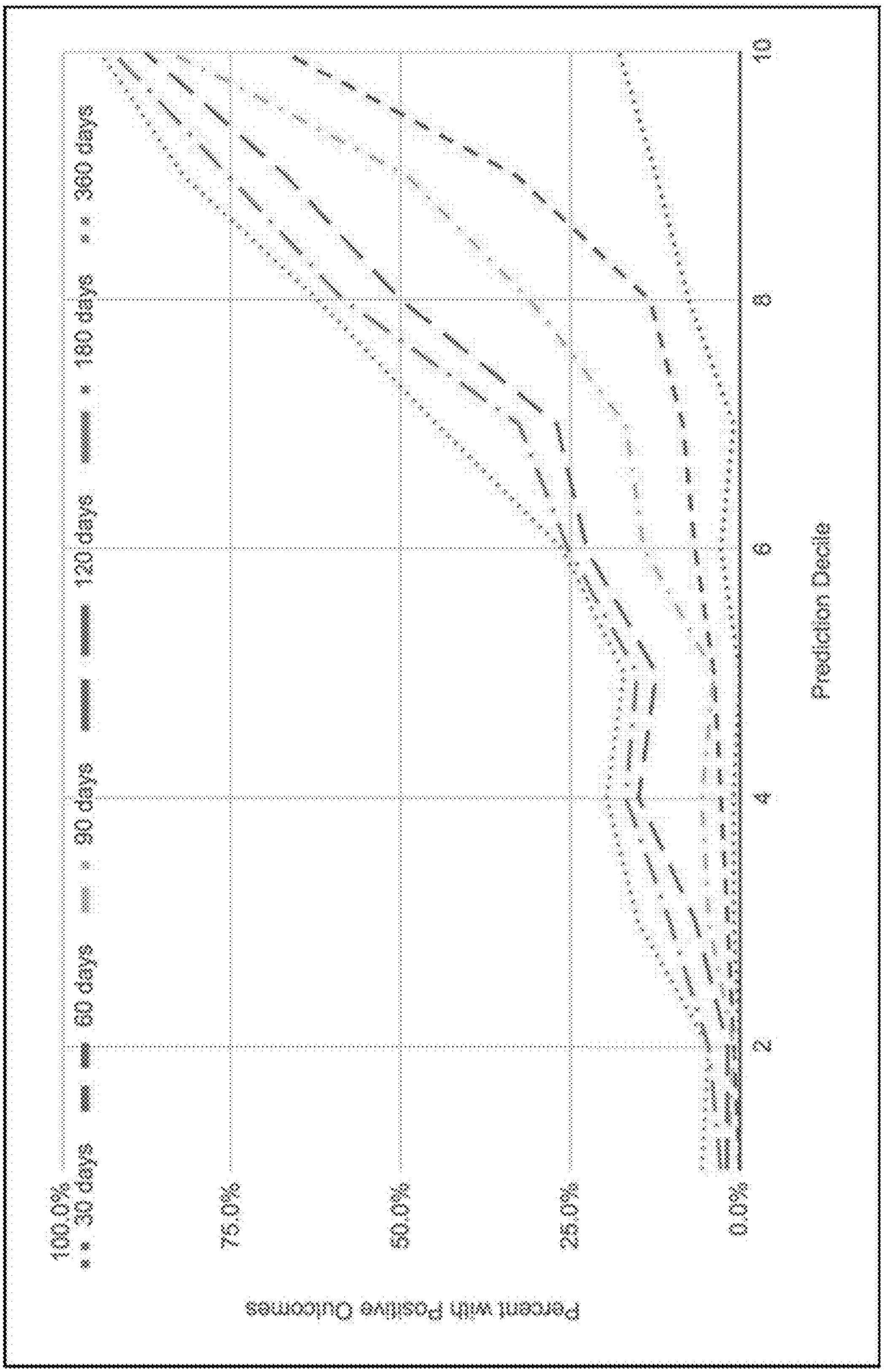
FIG. 4 is a graph of probability data related to positive outcomes of a CKD stage progression predictive machine learning algorithm, according to an example embodiment of the present disclosure.

Timeframe refers to number of days from prediction within which the positive outcome occurred FIG. 4 is a graph 400 of the probability data shown in Table 4, according to an example embodiment of the present disclosure. The graph 400 shows that as the decile increases, the percentage of patients with CKD stage progression increases for each timeframe of 30 days, 60 days, 90 days, 120 days, 180 days, and 360 days. Further, the graph 400 shows that for each decile, the probability of a stage progression increases with time. However, the greatest increases in probability occur in patients in the highest decile groups (deciles 7 to 10), which are more prone to stage progression initially.

The example CKD stage progression prediction model **118*a*** was compared to the known KDIGO two-factor model. The KDIGO model provides a guideline as to a frequency with which a patient should be assessed for CKD. The KDIGO model includes four different recommendations for the number of visits a patient should have per year based on the combination of GFR and albumin-to-creatinine ratio ("ACR"). The KDIGO provides a risk prediction model that correlates patients with a higher number of recommended visits to a higher risk level prediction.

In current clinical practice, the KDIGO two-factor model outputs a number of times a year a patient should be assessed in order to properly treat the current level of kidney disease, based upon a cross-section of the patient's GFR level and albumin-to-creatinine ratio (ACR). The two-factor model presents several limitations. Not only is it a simpler model that utilizes only two factors, but also, one of those two factors, GFR, presents its own limitations. Creatinine-based GFR estimation equations tend to produce an overestimation of true GFR in nephrotic syndrome in patients with hypoalbuminemia and uncertainty regarding whether CKD is present because of confounding by age, gender, race and creatinine production if it deviates substantially from normal.

The comparative analysis of the two-factor KDIGO model with CKD stage progression prediction model **118*a* demonstrates the strength of the model 118*a*** and the inherent actionability it provides to clinicians. Within the test data, the lab measurements to determine the recommended number of visits were available for many of the known sampled patients within 14 days of prediction. For these samples, each recommended number of visits group is broken out to show the results by decile from the stage progression prediction model, shown below in Table 5. Examination of this data reveals that the recommended number of visits appears to be correlated with the risk of stage progression. However, when broken out by the stage progression prediction model decile, it is shown that each level of recommended visits includes patients from different deciles that have different stage progression propensities. For example, for the recommended visits category of three, it is shown that this category contains patients from all of the different deciles and with different stage progression rates according to decile.

TABLE 5

Recommended Visits by CKD Stage Progression Prediction Decile

| | Recommended Visits | | | | | | | | | |
|---|---|---|---|---|---|---|---|---|---|---|
| Prediction | 1 | | 2 | | 3 | | 4+ | | Unknown | |
| Decile | n | % Positive | n | % Positive | n | % Positive | n | % Positive | n | % Positive |
| 1 | 74 | 1% | 12 | 0% | 5 | 0% | 0 | 0% | 16 | 6% |
| 2 | 61 | 2% | 20 | 5% | 4 | 0% | 0 | 0% | 21 | 0% |
| 3 | 31 | 10% | 27 | 4% | 10 | 10% | 0 | 0% | 38 | 5% |
| 4 | 23 | 9% | 18 | 17% | 9 | 0% | 2 | 50% | 55 | 18% |
| 5 | 3 | 0% | 17 | 18% | 12 | 17% | 1 | 0% | 73 | 11% |

TABLE 5-continued

Recommended Visits by CKD Stage Progression Prediction Decile

| Prediction | Recommended Visits | | | | | | | | | |
|---|---|---|---|---|---|---|---|---|---|---|
| | 1 | | 2 | | 3 | | 4+ | | Unknown | |
| Decile | n | % Positive | n | % Positive | n | % Positive | n | % Positive | n | % Positive |
| 8 | 5 | 0% | 16 | 31% | 13 | 15% | 2 | 0% | 70 | 24% |
| 7 | 1 | 0% | 9 | 22% | 17 | 29% | 7 | 14% | 73 | 29% |
| 8 | 1 | 100% | 6 | 100% | 25 | 60% | 1 | 100% | 73 | 41% |
| 9 | 0 | 0% | 0 | 0% | 15 | 60% | 7 | 86% | 84 | 67% |
| 10 | 0 | 0% | 0 | 0% | 13 | 92% | 26 | 85% | 68 | 88% |

Recommended Visits is based on the KDIGO guide to monitoring frequency
Prediction Decile is determined from the Stage Progression Prediction Model
n is the number of samples the model classified in each Prediction Decile
% Positive is the percent of samples with positive outcomes within 120 days from prediction In addition to the above, Table 6 below provides a more direct comparison between the KDIGO two-factor model and the CKD stage progression prediction model 118*a* by comparing the F1-scores for those samples where the recommended visits are known. At each time frame considered, the CKD stage progression prediction model 118*a* significantly outperforms the two-factor model.

TABLE 6

Model F1-score Comparison

| Timeframe (days) | Two-factor Model | CKD Stage Progression Prediction Model |
|---|---|---|
| 30 | 0.17 | 0.33 |
| 60 | 0.62 | 0.69 |
| 90 | 0.51 | 0.71 |
| 120 | 0.56 | 0.72 |
| 180 | 0.59 | 0.72 |
| 360 | 0.61 | 0.72 |

Timeframe refers to number of days from prediction within which the positive outcome occurred Tables 5 and 6 above demonstrate that, particularly among patients with values in the middle ranges, the dynamic, multifactorial CKD stage progression prediction model 118*a* provides meaningful risk differentiation beyond the KDIGO two-factor model. When looking at the patients recommended to have three office visits in a year, patients from all of the different deciles and with different stage-progression rates according to decile were grouped together by the KDIGO two-factor model. Following the guidance of the KDIGO model, all of these patients would have been treated the same by engaging in three assessments over the year. However, following the guidance of the CKD stage progression prediction model 118*a*, it is shown that 25% of the patients who fell in the three-visit category, were identified as very low risk by the example model 118*a* (deciles 1-4), and over 40% of the patients were identified as high-risk for stage change progression (deciles 8-10).

Thus, the decile analysis makes clear that the example CKD stage progression prediction model 118*a* more precisely stratifies patients in a way that would guide physicians towards the best level of care for each patient. Resource utilization would be more efficient, in that those patients in deciles 1-4, who were recommended three assessments, would be treated with less visits. Clinical care would improve for those patients in the higher deciles, as they would be treated more frequently. The patients in decile 10 would have already progressed in stage before their next visit (within 120 days) if they were being assessed three times per year, as recommended by the KDIGO two-factor model.

III. CKD URGENT-START DIALYSIS PREDICTION MODEL EMBODIMENT

This section discusses the properties and accuracy of the CKD urgent-start dialysis prediction model 118*b*. The CKD urgent-start dialysis prediction model 118*b* demonstrates strong performance in predicting risk of urgent-start dialysis over different timeframes of potential clinical follow-up, shown below in Table 7. The high sensitivity and PPV values indicate that a clinician has a high probability of identifying a potential urgent-start dialysis candidate in as short as 30 days and can take appropriate anticipatory steps, such as having a catheter placed for PD or ordering a home HD machine.

TABLE 7

CKD Urgent-start Dialysis Prediction Model - Machine Learning Metrics

| Timeframe (days) | Prevalence | Positive Predictive Value | Sensitivity | F1-score | AUC |
|---|---|---|---|---|---|
| 30 | 3.1% | 0.64 | 0.68 | 0.66 | 0.97 |
| 60 | 4.0% | 0.83 | 0.69 | 0.75 | 0.97 |
| 90 | 4.4% | 0.86 | 0.64 | 0.73 | 0.97 |
| 120 | 4.4% | 0.86 | 0.64 | 0.73 | 0.97 |
| 180 | 4.4% | 0.86 | 0.64 | 0.73 | 0.97 |
| 360 | 4.7% | 0.88 | 0.62 | 0.73 | 0.96 |

Timeframe refers to number of days from prediction within which the positive outcome occurred
Prevalence is the percent of samples with positive outcomes (i.e. urgent-start)
AUC—area under the curve; AUCs of 0.50 = chance level discriminative accuracy; 1.0 = perfect discriminative accuracy.

The prevalence (percent of samples with positive outcomes) within 90 days for the CKD urgent-start dialysis prediction model 118 is 4.4%. The decile analysis demonstrates that almost all of these urgent-start patients are identified within the top decile of risk, as shown below in Table 8. The machine learning metrics show that positive predictive value and F1-score can be even higher than implied by the decile analysis when focused on the riskiest portion within the top decile, but would come at some tradeoff in sensitivity.

TABLE 8

| CKD Urgent-start Dialysis Prediction Model - Percent with Positive Outcomes | | | | | | |
|---|---|---|---|---|---|---|
| | Timeframe | | | | | |
| Prediction Decile | 30 days | 60 days | 90 days | 120 days | 180 days | 360 days |
| 1 | 0.0% | 0.0% | 0.0% | 0.0% | 0.0% | 0.0% |
| 2 | 0.0% | 0.0% | 0.0% | 0.0% | 0.0% | 0.0% |
| 3 | 0.0% | 0.0% | 0.0% | 0.0% | 0.0% | 1.0% |
| 4 | 0.0% | 0.0% | 0.0% | 0.0% | 0.0% | 0.0% |
| 5 | 0.0% | 0.0% | 0.0% | 0.0% | 0.0% | 0.0% |
| 6 | 1.0% | 1.0% | 1.0% | 1.0% | 1.0% | 1.0% |
| 7 | 1.0% | 1.0% | 1.0% | 1.0% | 1.0% | 1.0% |
| 8 | 0.0% | 0.0% | 1.0% | 1.0% | 1.0% | 2.0% |
| 9 | 1.0% | 1.0% | 1.0% | 1.0% | 1.0% | 1.0% |
| 10 | 29.0% | 38.0% | 41.0% | 41.0% | 41.0% | 43.0% |

Timeframe refers to number of days from prediction within which the positive outcome occurred

IV. CKD MACHINE LEARNING USAGE EMBODIMENT

Returning to FIG. 1, the analytics processor 106 of the management server 102 receives the CKD stage progression prediction model 118*a* and/or the CKD urgent-start dialysis prediction model 118*b* from the model generator 104. The analytics processor 106 uses the models 118 to provide clinical decision support for clinicians treating patients with CKD. The analytics processor 106 may store the models to a memory device 130.

In some embodiments, the analytics processor 106 hosts a website or other Internet accessible interface, such as an application programmable interface ("API") that enables clinician devices 132 to submit patient characteristics and receive predicted outcomes. The clinician device 132 may include an application 134, such as a web browser or an 'app' for accessing the analytics processor 106.

In some examples, the clinician device 132 and the analytics processor 106 may be connected to a system hub (not shown). Alternatively, the system hub may be included as part of the analytics processor 106 and include a service portal, an enterprise resource planning system, a web portal, a business intelligence portal, a HIPAA compliant database, and electronic medical records databases.

A webpage or form provided by the analytics processor 106 may prompt a clinician for patient characteristic data 136. In other examples, the application 134 may enable a clinician to specify a patient identifier, which causes the application 134 to transmit information from the patient's EMR (as patient characteristic data 136) to the analytics processor 106.

Figure 5:
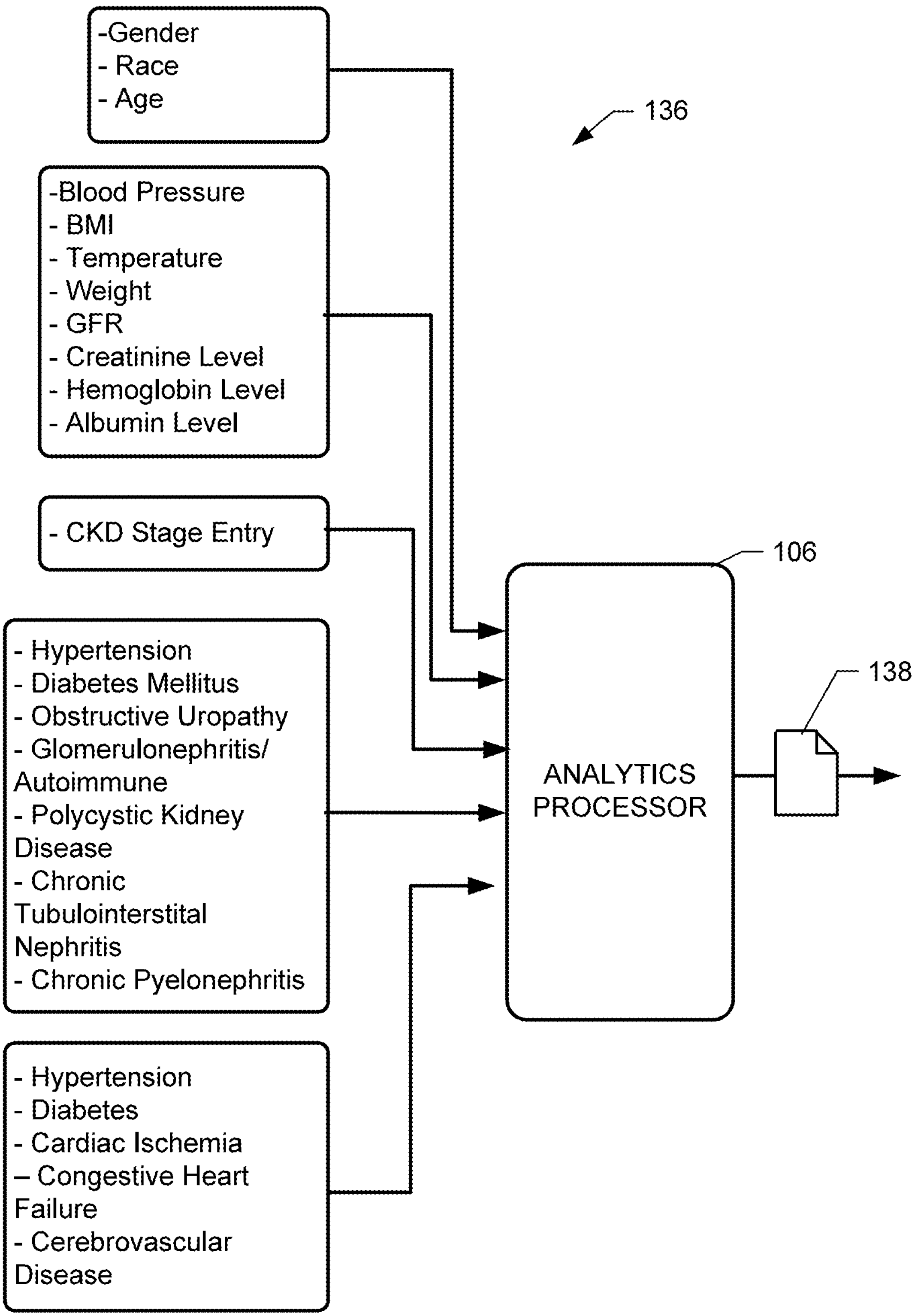
FIG. 5 is a diagram of example patient characteristic data received by the analytics processor of FIG. 1, according to an example embodiment of the present disclosure.

FIG. 5 is a diagram of example patient characteristic data 136 received by the analytics processor 106, according to an example embodiment of the present disclosure. The patient characteristic data 136 may include demographic data such as age, gender, and race. The patient characteristic data 136 may also include physiological data, such as blood pressure, BMI, temperature, weight, GFR, creatinine levels, hemoglobin levels, and albumin levels. In some instances, the patient characteristic data 136 may include a CKD stage entry. Otherwise, the analytics processor 106 may determine a patient's CKD stage from their GFR and/or albumin data. The patient characteristic data 136 may further include a diagnosed cause of CKD including hypertension, diabetes mellitus, obstructive uropathy, glomerulonephritis/autoimmune, polycystic kidney disease, chronic tubulointerstitial nephritis, or chronic pyelonephritis. Moreover, the patient characteristic data 136 may include health history such as hypertension, diabetes, cardiac ischemia, congestive heart failure, or cerebrovascular disease.

It should be appreciated that less or additional patient characteristic data 136 may be used by the analytics processor 106. For example, the analytics processor 106 may be configured to analyze a patient's characteristic data 136 having only a small amount of data to submit to the machine learning models 118. The analytics processor 106 may transit an error message to the clinician device 132 if a sufficient amount of patient characteristic data 136 has not been provided (e.g., missing GFR data).

After receiving the data 136, the analytics processor 106 performs a CKD predictive analysis using the CKD stage progression prediction model 118*a* and/or the CKD urgent-start dialysis prediction model 118*b*. To perform the analysis, the analytics processor 106 may classify the patient undergoing analysis into a closest matching prediction decile for the CKD entry stage of the patient. To perform this operation, the analytics processor 106 compares the patient characteristic data 136 of the patient under analysis to classifications of patient characteristic data 112 provided in the respective model 118. This includes identifying the current CKD stage as a starting point for the models 118. This identification may include performing a comparison for each factor/characteristic of the patient to the modeled factors/characteristics (including derivative factors/characteristics) at the same CKD stage. The models 118 may assign a patient to, for example, one or more deciles based on the comparison. The analytics processor 106 uses the probabilities of positive outcomes for each model 118 to determine percentage likelihoods (or probabilities) that the patient undergoing analysis will, for example, progress to a next CKD stage (or need urgent start dialysis) for the discrete timeframes based on the closest matching prediction decile.

Figure 6:
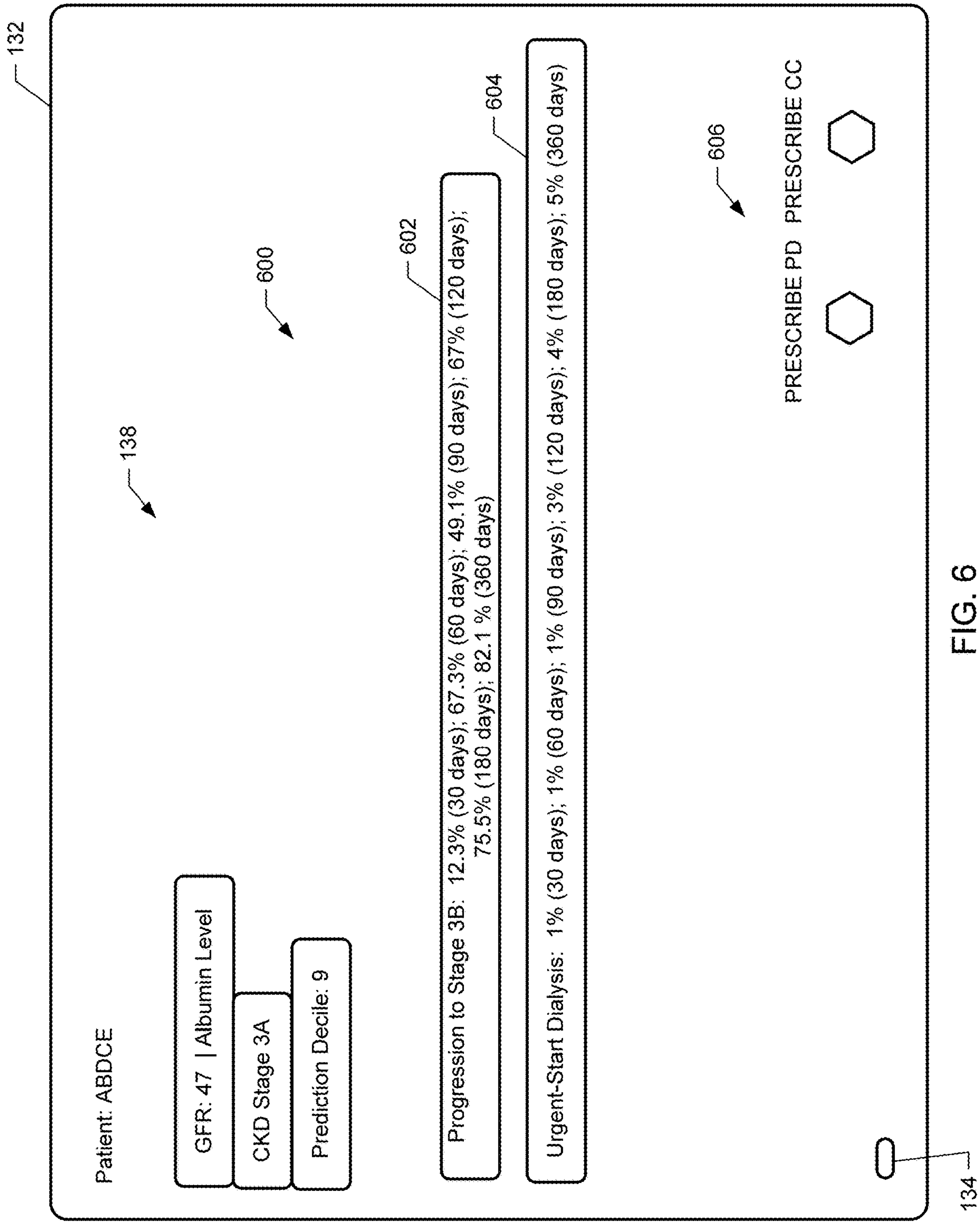
FIG. 6 is a diagram of a user interface displayed via an application on a clinician device showing a machine learning model output from the analytics processor of FIG. 1, according to an example embodiment of the present disclosure.

The analytics processor 106 creates a report 138 that provides the predicted positive outcomes for the patient under analysis for the modeled discrete timeframes. The analytics processor 106 may display information from the report 138 in a user interface, such as a webpage or interface of the application 134 of the clinician device 132. FIG. 6 is a diagram of a user interface 600 displayed via the application 134 on the clinician device 132 showing information from the report 138, according to an example embodiment of the present disclosure. In some embodiments, a clinician may also use the interface 600 for specifying a patient identifier or providing a patient's characteristic data for generating the report 138 via the analytics processor 106.

The example user interface 600 includes a patient identifier and at least some patent characteristic data 136 including a GFR and albumin level. The user interface 600 also includes at least some information related to the processing of the patient characteristic data within the models 118 including an estimated CKD stage and a prediction decile. The user interface 600 further includes a summary of the output from the machine learning models 118. A first output 602 provides a rate and probability of progression from CKD Stage 3A to CKD Stage 3B for discrete timeframes. A second output 604 provides a probability that the patient under analysis will need urgent start dialysis within the specified timeframes. A clinician reviews the first output 602 and the second output 604 to determine potential treatments for a patient to slow the progression of the patient's CKD.

In some embodiments, the analytics processor 106 may display an option 606 in the user interface 600 for prescribing a treatment. In an example, the analytics processor 106 may determine recommended treatments for selection based on a patient's CKD stage, probabilities of CKD progression, estimated rate of CKD progression, and probability for needing urgent start dialysis. For instance, the analytics processor 106 may provide options for medication and/or lifestyle changes for patients in a CKD Stage 3A or 3B with a progression probability less than 25% and a need for urgent start of dialysis less than 10%. By comparison, the analytics processor 106 may be configured to provide a recommendation for a PD treatment or a critical care ("CC") treatment if the patient is in CKD Stage 5, and a greater than 50% probability to progressing to Stage 5 within 180 days, and/or has a greater than 35% change of needing urgent dialysis within 90 days.

For illustration purposes (unrelated to the data in the outputs 602 and 604), the user interface 600 includes an option 606 for prescribing a PD treatment and/or a CC treatment for a patient. Selection of the PD treatment, for example, causes the analytics processor 106 to display a form or webpage via the application 134 for entering PD prescription parameters, including dextrose level, treatment duration, treatment frequency, treatment dialysis volume, expected UF to remove, etc. In some instances, the selection of the PD treatment option may also enable a clinician to schedule a medical procedure for inserting a catheter into the patient.

Figure 7:
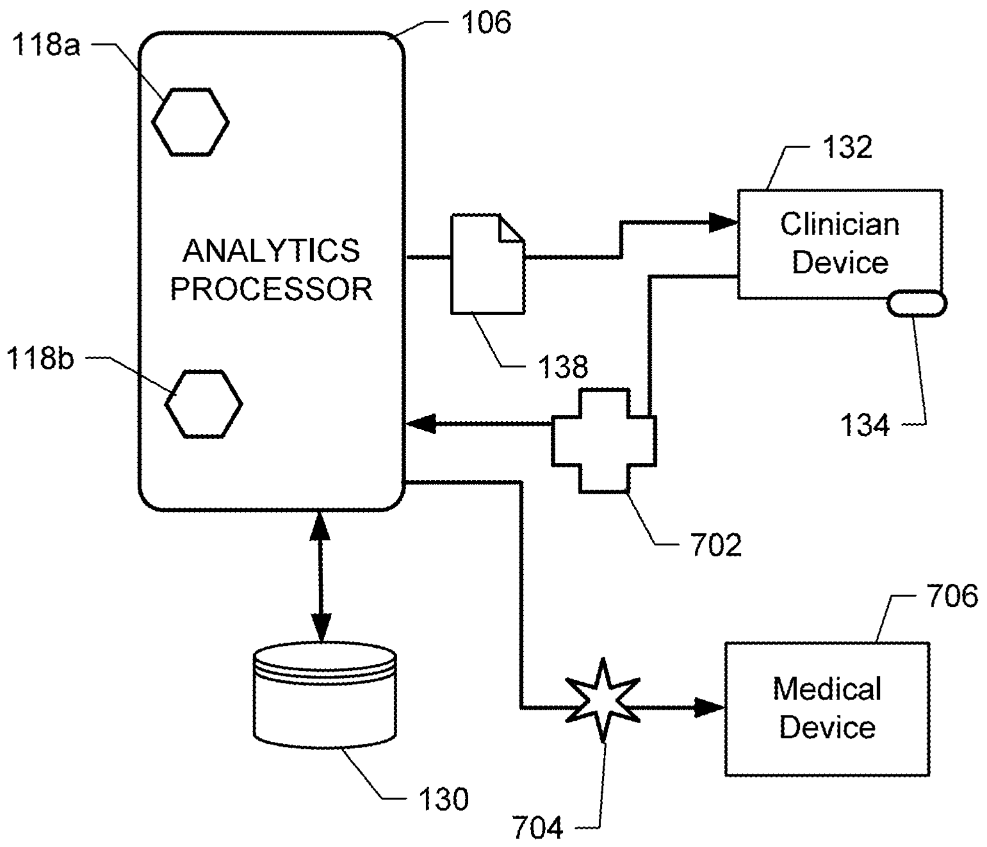
FIG. 7 is a diagram illustrative of a process flow related to a clinician using an application to enter treatment parameters for programming a medical device based on the machine learning model output of FIG. 6, according to an example embodiment of the present disclosure.

FIG. 7 shows a diagram where a clinician uses the application 134 to enter treatment parameters 702, which are transmitted to the analytics processor 106. Reception of the treatment parameters 702 may cause the analytics processor 106 to remotely program or create a therapy program 704 for a medical device 706. The analytics processor 106 may provide the therapy program 704 after the medical device 706 is identified and/or configured for the patient under analysis.

A prescribed treatment, prescription, or therapy program 704 corresponds to one or more parameters that define how the medical device 706 is to operate to administer a treatment to a patient. For a peritoneal dialysis therapy, the parameters may specify an amount (or rate) of fresh dialysis fluid to be pumped into a peritoneal cavity of a patient, an amount of time the fluid is to remain in the patient's peritoneal cavity (i.e., a dwell time), and an amount (or rate) of used dialysis fluid and ultrafiltration ("UF") that is to be pumped or drained from the patient after the dwell period expires. For a treatment with multiple cycles, the parameters may specify the fill, dwell, and drain amounts for each cycle and the total number of cycles to be performed during the course of a treatment (where one treatment is provided per day or separate treatments are provided during the daytime and during nighttime). In addition, the parameters may specify dates/times/days (e.g., a schedule) in which treatments are to be administered by the medical fluid delivery machine. Further, parameters of a prescribed therapy may specify a total volume of dialysis fluid to be administered for each treatment in addition to a concentration level of the dialysis fluid, such as a dextrose level.

The medical device 706 of FIG. 7 may include a renal failure therapy machine for treating kidney failure or reduced kidney function. Through dialysis, the renal failure machine removes waste, toxins and excess water from a patient that normal functioning kidneys would otherwise remove. For peritoneal dialysis, the medical device 706 infuses a dialysis solution, also called dialysis fluid, into a patient's peritoneal cavity via a catheter. The dialysis fluid contacts the peritoneal membrane of the peritoneal cavity. Waste, toxins and excess water pass from the patient's bloodstream, through the peritoneal membrane and into the dialysis fluid due to diffusion and osmosis, i.e., an osmotic gradient occurs across the membrane. An osmotic agent in the dialysis fluid provides the osmotic gradient. The used or spent dialysis fluid is drained from the patient, removing waste, toxins and excess water from the patient. This cycle is repeated, e.g., multiple times.

There are various types of peritoneal dialysis therapies, including continuous ambulatory peritoneal dialysis ("CAPD"), automated peritoneal dialysis ("APD"), and tidal flow dialysis and continuous flow peritoneal dialysis ("CFPD"). CAPD is a manual dialysis treatment. Here, the patient manually connects an implanted catheter to a drain to allow used or spent dialysate fluid to drain from the peritoneal cavity. The patient then connects the catheter to a bag of fresh dialysis fluid to infuse fresh dialysis fluid through the catheter and into the patient. The patient disconnects the catheter from the fresh dialysis fluid bag and allows the dialysis fluid to dwell within the peritoneal cavity, wherein the transfer of waste, toxins and excess water takes place. After a dwell period, the patient repeats the manual dialysis procedure, for example, four times per day, each treatment lasting about an hour. Manual peritoneal dialysis requires a significant amount of time and effort from the patient, leaving ample room for improvement.

Automated peritoneal dialysis ("APD") is similar to CAPD in that the dialysis treatment includes drain, fill and dwell cycles. APD machines, however, perform the cycles automatically, typically while the patient sleeps. APD machines free patients from having to perform the treatment cycles manually and from having to transport supplies during the day. APD machines connect fluidly to an implanted catheter, to a source or bag of fresh dialysis fluid and to a fluid drain. APD machines pump fresh dialysis fluid from a dialysis fluid source, through the catheter and into the patient's peritoneal cavity. APD machines also allow for the dialysis fluid to dwell within the cavity and for the transfer of waste, toxins and excess water to take place. The source may include multiple sterile dialysis fluid bags.

APD machines pump used or spent dialysate from the peritoneal cavity, though the catheter, and to the drain. As with the manual process, several drain, fill and dwell cycles occur during dialysis. A "last fill" occurs at the end of APD and remains in the peritoneal cavity of the patient until the next treatment.

Another type of kidney failure therapy that may be performed by the medical device 706 is Hemodialysis ("HD"), which in general uses diffusion to remove waste products from a patient's blood. A diffusive gradient occurs across the semi-permeable dialyzer between the blood and an electrolyte solution called dialysate or dialysis fluid to cause diffusion.

Hemofiltration ("HF") is an alternative renal replacement therapy that relies on a convective transport of toxins from the patient's blood. HF is accomplished by adding substitution or replacement fluid to the extracorporeal circuit during treatment (typically ten to ninety liters of such fluid). The substitution fluid and the fluid accumulated by the patient in between treatments is ultrafiltered over the course of the HF treatment, providing a convective transport mechanism that is particularly beneficial in removing middle and large molecules (in hemodialysis there is a small amount of waste removed along with the fluid gained between dialysis sessions, however, the solute drag from the removal of that ultrafiltrate is not enough to provide convective clearance).

Hemodiafiltration ("HDF") is a treatment modality that combines convective and diffusive clearances. HDF uses dialysis fluid flowing through a dialyzer, similar to standard hemodialysis, to provide diffusive clearance. In addition, substitution solution is provided directly to the extracorporeal circuit, providing convective clearance.

Most HD (HF, HDF) treatments occur in centers. A trend towards home hemodialysis ("HHD") exists today in part because HHD can be performed daily, offering therapeutic benefits over in-center hemodialysis treatments, which occur typically bi- or tri-weekly. Studies have shown that frequent treatments remove more toxins and waste products than a patient receiving less frequent but perhaps longer treatments. A patient receiving treatments more frequently does not experience as much of a down cycle as does an in-center patient, who has built-up two or three days' worth of toxins prior to treatment. In certain areas, the closest dialysis center can be many miles from the patient's home causing door-to-door treatment time to consume a large portion of the day. HHD may take place overnight or during the day while the patient relaxes, works or is otherwise productive.

The examples described in connection with the medical device 706 are applicable to any medical fluid delivery system that delivers a medical fluid, such as blood, dialysis fluid, substitution fluid or an intravenous drug ("IV"). The examples are particularly well suited for kidney failure therapies, such as all forms of hemodialysis ("HD"), hemofiltration ("HF"), hemodiafiltration ("HDF"), continuous renal replacement therapies ("CRRT") and peritoneal dialysis ("PD"), referred to herein collectively or generally individually as a prescribed therapy or program. The medical fluid delivery machines may alternatively be a drug delivery or nutritional fluid delivery device, such as a large volume peristaltic type pump or a syringe pump. The machines described herein may be used in home settings.

Figure 8:
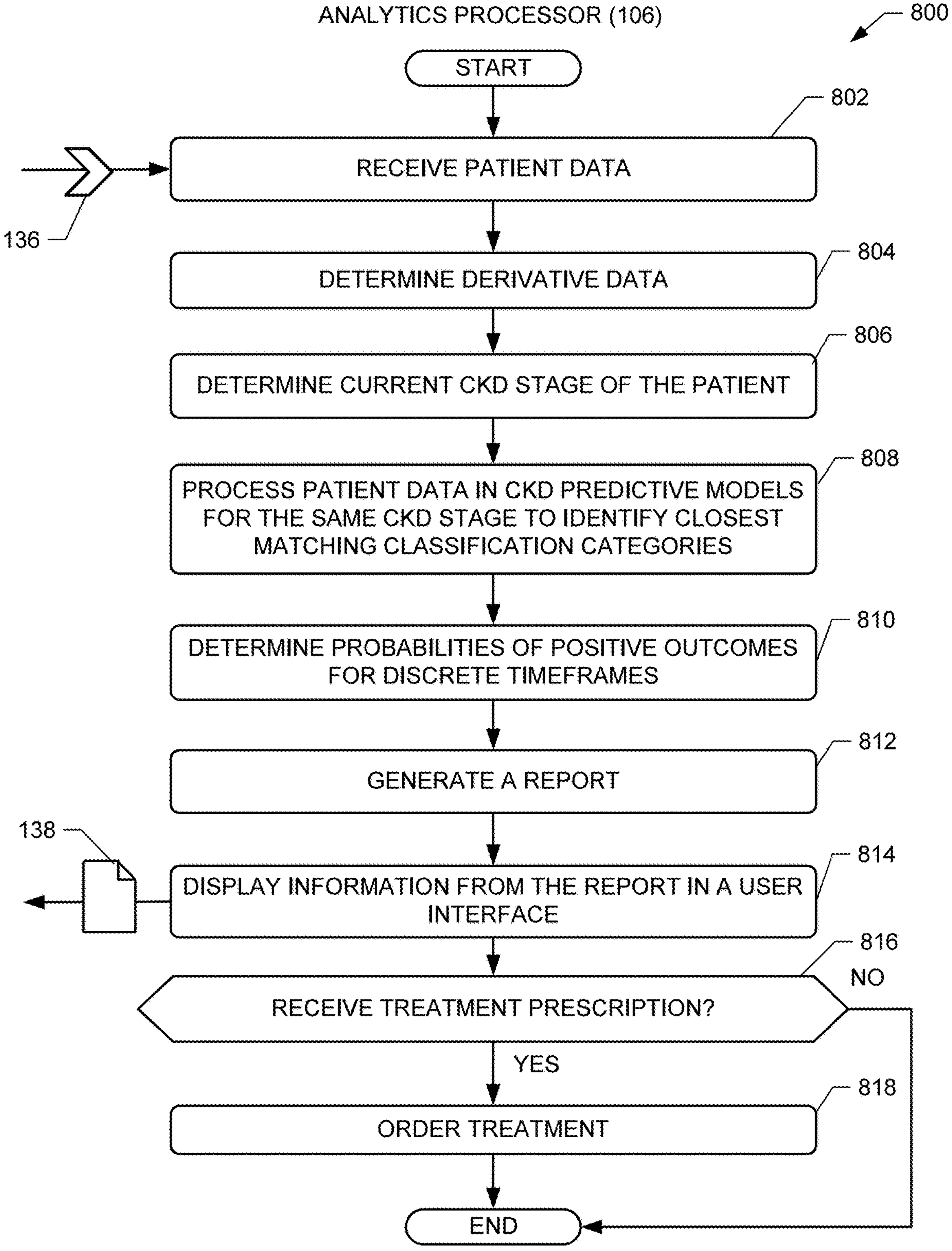
FIG. 8 is a flow diagram of an example procedure for analyzing a patient's characteristic data via the CKD predictive machine learning models disclosed herein, according to an example embodiment of the present disclosure.

FIG. 8 is a flow diagram of an example procedure 800 for analyzing a patient's characteristic data 136 via the CKD predictive machine learning models 118 disclosed herein, according to an example embodiment of the present disclosure. Although the procedure 800 is described with reference to the flow diagram illustrated in FIG. 8, it should be appreciated that many other methods of performing the steps associated with the procedure 800 may be used. For example, the order of many of the blocks may be changed, certain blocks may be combined with other blocks, and many of the blocks described may be optional. In an embodiment, the number of blocks may be changed based on data preprocessing and filtering and/or the types of developed machine learning models. The actions described in the procedure 800 are specified by one or more instructions that are stored in a memory device, and may be performed among multiple devices including, for example the analytics processor 106.

The example procedure 800 begins when the analytics processor 106 receives patient characteristic data 136 via an application 134 on a clinician device 132 (block 802). The data 136 may be received via one or more APIs of the analytics processor 106, which are linked to inputs of the CKD stage progression prediction model 118*a* and/or the CKD urgent-start dialysis prediction model 118*b*. In some embodiments, the analytics processor 106 determines derivative characteristic data from the patient characteristic data, such as a patient's CKD stage and/or albumin-to-creatinine ratio (block 804). The analytics processor 106 identifies the patient's current CKD stage, which is used as an input to the CKD stage progression prediction model 118*a* and/or the CKD urgent-start dialysis prediction model 118*b* for comparison with classified data at the same CKD stage (block 806).

The example analytics processor 106 then processes the patent characteristic data 136, the derivative data, and/or CKD stage of the patient in the CKD stage progression prediction model 118*a* and/or the CKD urgent-start dialysis prediction model 118*b* to identify closest matching classification categories or deciles (block 808). As part of the comparison, the analytics processor 106 matches each patient characteristic to the same classified characteristic and uses one or more best-fit analyses to determine a classification for the patient under analysis. For example, the patient's blood pressure, GFR, BMI, gender, age, and albumin values are compared to distributions for the different classifications to determine a distance from a normal distribution or mean values. Differences may be summed for each of the characteristics or factors, where a category or decile corresponding to a lowest difference is selected for a patient. In other instances, the analytics processor 106 uses a weighted-averaging routine to compile probabilities from different classification categories for each factor such that the probability outcome is a combined mixture of the different classification categories based on a closeness to the patient's characterization data or factors.

The analytics processor 106 uses the matching and/or comparison to determine outcome probabilities for the patient under analysis (block 810). This includes determining a rate and stage progression probability from the CKD stage progression prediction model 118*a* and/or a probability the patient will need dialysis from the CKD urgent-start dialysis prediction model 118*b*. The models 118*a* and 118*b* generate the probabilities for specified discrete timeframes including, for example, 30 days, 60 days, 90 days, 120 days, 180 days, 360 days, etc.

The analytics processor 106 then generates a report 138 using the outputs from the models 118*a* and 118*b* (block 812). The analytics processor 106 causes the report 138 to be displayed in a user interface of the application 134 on the clinician device 132 (block 814). The analytics process 106 may next determine if a treatment prescription is received (block 816). If a treatment prescription is not received, the example procedure 800 ends until a CKD analysis is needed for another patient or again for the same patient. However, if a treatment prescription is received, the analytics processor 106 causes a treatment to be ordered (block 818). This may include transmitting an order for a dialysis machine or other medical device, an order for placement of a catheter, a medication order, and/or an order for an application to assist a patient in changing their lifestyle. The order may also include a message that causes a dialysis machine or other medical device to begin a treatment. The example procedure 800 ends until a CKD analysis is needed for another patient or again for the same patient.

V. PREDICTIVE CKD MACHINE LEARNING MODEL PERFORMANCE

As shown above, the multifactorial machine learning models 118*a* and 118*b* exhibit strong predictive capability. Not only are the models 118*a* and 118*b* able to utilize time-dependent data, such as laboratory values that change over time, but they are also able to consider as many feature characteristics as the dataset presents in order to assess patient risk. A large number of factors and patient characteristics are considered by the models 118 in producing the algorithms. Different factors presented themselves as the most influential in determining patient risk for each model. For instance, GFR, creatinine, blood pressure, and BMI were among the top inputs that factor into identifying patients' risk for the CKD stage progression prediction model 118. Whereas factors such as hemoglobin, albumin, and creatinine appeared towards the top of the list for the CKD urgent-start dialysis prediction model 118*b*

The output of the CKD stage progression prediction model 118 can be used by the analytics processor 106 to guide clinicians to the level of care that patients would most benefit from to slow their progression to the next CKD stage. As seen in Table 4, patients that the model places in the higher deciles of predicted risk did progress in stage more quickly. Eighty-eight percent of patients predicted to progress in stage within 120 days, did, in fact, progress. Thus, a clinician, using the CKD stage progression prediction model 118, has a high level of confidence in treating patients based upon their risk level. These patients require sooner, more frequent office visits i to address their symptoms and slow the disease progression as much as possible.

Moreover, since CKD stage progression prediction model 118*a* is based on many factors, it has been determined to be quite robust handling missing or incomplete data. Even when the recommended visits data is unknown, due to missing ACR values, the CKD stage progression prediction model 118*a* continues to effectively differentiate risk. The above-decile analysis discussed in connection with Tables 5 and 6 demonstrates with more accuracy the predicted CKD stage progression rate and enables physicians to treat higher-risk patients more aggressively and to refrain from using resources for assessing lower-risk patients more than is necessary.

The CKD urgent-start dialysis prediction model 118*b* proves to accurately identify patients at high-risk of an urgent-start. As seen above in Table 8, the 41% of patients predicted to be at high risk for urgent-start dialysis (decile 10) experienced one rapidly, within 30-90 days. Because the model exhibits high sensitivity and PPV, a care provider has a high probability of identifying a potential urgent-start dialysis candidate in as short as 30 days and can take appropriate anticipatory steps. An emergency, unscheduled dialysis treatment may cost up to 20 times more than a regularly scheduled treatment. Therefore, a decrease in the number of emergency treatments result in cost-savings, along with an improvement in patient care.

VI. CONCLUSION

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. A system for estimating a patient's chronic kidney disease ("CKD") progression, the system comprising:

a memory device storing patient characteristic data for a patient undergoing analysis, the patient characteristic data including demographic/physiological data, a CKD entry stage, a diagnosed cause of CKD, and a health history;

an ensemble machine learning algorithm trained to predict a progression to a next stage of CKD and a timeframe of the progression to the next stage of CKD, the ensemble machine learning algorithm trained to have prediction decile classifiers that each includes (i) percentages of known patients that progressed from one moderate CKD stage to a next moderate or severe CKD stage for discrete timeframes, and (ii) known patient characteristic data that corresponds to the known patients, the known patient characteristic data being used to train the ensemble machine learning algorithm and including demographic/physiological data for the known patients, a diagnosed cause of CKD, a health history, and a classification of a positive or a negative result related to CKD stage progression, wherein each prediction decile for different CKD stages is assigned a probability of a positive outcome for CKD progression for each of the discrete timeframes using (i); and an analytics processor communicatively coupled to the memory device, the analytics processor in conjunction with the ensemble machine learning algorithm configured to:

input the patient characteristic data for the patient undergoing analysis into the ensemble machine learning algorithm, using the ensemble machine learning algorithm to classify the patient undergoing analysis into a closest matching prediction decile for the CKD entry stage of the patient by comparing the patient characteristic data of the patient undergoing analysis to classifications of the known patient characteristic data provided in the ensemble machine learning algorithm, determine a probability that the patient undergoing analysis will progress to a next moderate or severe CKD stage for each of the discrete timeframes using the assigned probability of the closest matching prediction decile, and display, via a user interface, the probability that the patient undergoing analysis will progress to the next moderate or severe CKD stage for the discrete timeframes.

2. The system of claim 1, wherein the demographic/physiological data includes at least one of a gender, a race, an age, a body-mass index, a blood pressure, a creatinine level, a glomerular filtration rate ("GFR"), a hemoglobin level, or an albumin level.

3. The system of claim 1, wherein the diagnosed cause of CKD includes at least one of hypertension, diabetes mellitus, obstructive uropathy, glomerulonephritis/autoimmune, polycystic kidney disease, chronic tubulointerstitial nephritis, or chronic pyelonephritis.

4. The system of claim 1, wherein the health history includes at least one of hypertension, diabetes, cardiac ischemia, congestive heart failure, or cerebrovascular disease.

5. The system of claim 1, wherein the percentages of known patients that progressed from one moderate CKD stage to a next moderate or severe CKD stage are determined using patient population data including patient characteristic data, known CKD progression data, and exit results.

6. The system of claim 5, wherein the exit results include at least one of a dialysis therapy, a renal replacement therapy ("RRT"), death, kidney transplant, or palliative care.

7. The system of claim 5, wherein the known CKD progression data identifies stage progressions based on a change of an estimated glomerular filtration rate ("GFR") that is associated with a different moderate or severe CKD stage, or at least a 25% change of the estimated GFR from a previously known GFR.

8. The system of claim 1, wherein the CKD entry stage of the patient is based on at least one of an estimated GFR of the patient or a length of time the patient has been experiencing proteinuria.

9. The system of claim 1, wherein the discrete timeframes include at least one of 30 days, 60 days, 90 days, 120 days, 180 days, and 360 days.

10. The system of claim 1, wherein the moderate or severe CKD stages include Stage 3A with a GFR between 45 to 59 mL/min, Stage 3B with a GFR between 30 to 44 mL/min, Stage 4 with a GFR between 15 to 29 mL/min, and Stage 5 with a GFR less than 15 mL/min.

11. The system of claim 1, wherein the ensemble machine learning algorithm includes prediction decile classifiers that each includes percentages of known patients that progressed from one minor CKD stage to a next moderate or severe CKD stage for discrete timeframes, and wherein the CKD entry stage includes at least one of Stage 1 with a GFR greater than 90 mL/min, Stage 2 with a GFR between 60 and 89 mL/min, Stage 3A with a GFR between 45 to 59 mL/min, Stage 3B with a GFR between 30 to 44 mL/min, or Stage 4 with a GFR between 15 to 29 mL/min.

12. The system of claim 1, wherein the user interface is displayed on a clinician computer.

13. A system for estimating a likelihood a patient with chronic kidney disease ("CKD") will need an urgent start of dialysis, the system comprising:

a memory device storing patient characteristic data for a patient undergoing analysis, the patient characteristic data including demographic/physiological data, a CKD entry stage, a diagnosed cause of CKD, and a health history;

an ensemble machine learning algorithm trained to predict a likelihood the patient undergoing analysis will need an urgent start of dialysis, the ensemble machine learning algorithm trained to have prediction decile classifiers that each includes (i) percentages of known patients that needed an urgent start of dialysis for discrete timeframes, and (ii) known patient characteristic data that corresponds to the known patients, the known patient characteristic data being used to train the ensemble machine learning algorithm and including demographic/physiological data for the known patients, a diagnosed cause of CKD, a health history, and a classification of a positive or a negative result related to an urgent start of dialysis, wherein each prediction decile for different CKD stages is assigned a probability of a positive outcome for an urgent start of dialysis for each of the discrete timeframes using (i); and an analytics processor communicatively coupled to the memory device, the analytics processor in conjunction with the ensemble machine learning algorithm configured to:

input the patient characteristic data for the patient undergoing analysis into the ensemble machine learning algorithm, using the ensemble machine learning algorithm to classify the patient undergoing analysis into a closest matching prediction decile for the CKD entry stage of the patient by comparing the patient characteristic data of the patient undergoing analysis to classifications of the known patient characteristic data provided in the ensemble machine learning algorithm, determine probabilities that the patient undergoing analysis will need an urgent start of dialysis for the discrete timeframes using the assigned probability of the closest matching prediction decile, and display, via a user interface, the probabilities that the patient undergoing analysis will need the urgent start of dialysis for the discrete timeframes.

14. The system of claim 13, wherein the demographic/physiological data includes at least one of a gender, a race, an age, a body-mass index, a blood pressure, a creatinine level, a glomerular filtration rate ("GFR"), a hemoglobin level, or an albumin level.

15. The system of claim 13, wherein the diagnosed cause of CKD includes at least one of hypertension, diabetes mellitus, obstructive uropathy, glomerulonephritis/autoimmune, polycystic kidney disease, chronic tubulointerstitial nephritis, or chronic pyelonephritis.

16. The system of claim 13, wherein the health history includes at least one of hypertension, diabetes, cardiac ischemia, congestive heart failure, or cerebrovascular disease.

17. The system of claim 13, wherein the percentages of known patients that needed an urgent start of dialysis are determined using patient population data including patient characteristic data, known CKD progression data, and exit results.

18. The system of claim 17, wherein CKD stages of the known CKD progression data include Stage 1 with a GFR greater than 90 mL/min, Stage 2 with a GFR between 60 and 89 mL/min, Stage 3A with a GFR between 45 to 59 mL/min, Stage 3B with a GFR between 30 to 44 mL/min, Stage 4 with a GFR between 15 to 29 mL/min, and Stage 5 with a GFR less than 15 mL/min.

19. The system of claim 13, wherein the analytics processor is configured to:

receive an indication to start a dialysis treatment; and cause the dialysis treatment to be prepared for the patient.

20. The system of claim 19, further comprising a dialysis machine configured to perform the dialysis treatment for the patient.

* * * * *